United States Patent
Spargo et al.

(10) Patent No.: US 12,251,384 B1
(45) Date of Patent: **\*Mar. 18, 2025**

(54) PARTICULATE COMPOSITION

(71) Applicant: Verona Pharma PLC, Cardiff (GB)

(72) Inventors: Peter Lionel Spargo, Cardiff (GB); Kevin Stephen Turner, Cardiff (GB)

(73) Assignee: Verona Pharma PLC, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/949,105

(22) Filed: Nov. 15, 2024

Related U.S. Application Data

(63) Continuation of application No. 18/753,759, filed on Jun. 25, 2024, now Pat. No. 12,194,045.

(60) Provisional application No. 63/550,786, filed on Feb. 7, 2024, provisional application No. 63/550,792, filed on Feb. 7, 2024.

(30) Foreign Application Priority Data

Jun. 26, 2023 (GB) ...................................... 2309605

(51) Int. Cl.
*A61K 31/519* (2006.01)
*A61K 9/00* (2006.01)

(52) U.S. Cl.
CPC .......... *A61K 31/519* (2013.01); *A61K 9/0073* (2013.01)

(58) Field of Classification Search
CPC .... A61K 31/519; A61K 47/02; A61K 9/0078; A61K 2300/00; A61K 9/0075; A61K 9/10; A61K 31/40; A61K 31/513; A61K 31/517; A61K 45/06; A61K 47/12; A61K 47/14; A61K 47/26; A61K 9/08; A61K 9/145; A61K 9/1682; A61P 11/00; A61P 11/08

See application file for complete search history.

(56) References Cited

U.S. PATENT DOCUMENTS

| | | | |
|---|---|---|---|
| 4,482,556 A | 11/1984 | Lal et al. | |
| 5,378,818 A | 1/1995 | Mayer et al. | |
| 5,985,878 A | 11/1999 | Stokbroekx et al. | |
| 6,794,391 B2 | 9/2004 | Oxford et al. | |
| 7,105,663 B2 | 9/2006 | Oxford et al. | |
| 7,378,424 B2 | 5/2008 | Oxford et al. | |
| 8,221,772 B2 | 7/2012 | Johnson et al. | |
| 8,242,127 B2 | 8/2012 | Oxford et al. | |
| 9,062,047 B2 | 6/2015 | Walker et al. | |
| 9,700,558 B2 | 7/2017 | Walker et al. | |
| 9,717,732 B2 | 8/2017 | Walker et al. | |
| 9,956,171 B2 | 5/2018 | Spargo et al. | |
| 10,463,665 B2 | 11/2019 | Spargo et al. | |
| 10,471,063 B2 | 11/2019 | Walker et al. | |
| 10,710,998 B2 | 7/2020 | Spargo | |
| 10,864,213 B2 | 12/2020 | Abbott-Banner et al. | |
| 10,945,950 B2 | 3/2021 | Spargo et al. | |
| 11,491,155 B2 | 11/2022 | Spargo et al. | |
| 11,759,467 B2 | 9/2023 | Abbott-Banner et al. | |
| 12,168,011 B2 | 12/2024 | Spargo et al. | |
| 2003/0036542 A1 | 2/2003 | Oxford et al. | |
| 2003/0229108 A1 | 12/2003 | De Belin et al. | |
| 2004/0076668 A1 | 4/2004 | Berchielli et al. | |
| 2004/0171828 A1 | 9/2004 | Oxford et al. | |
| 2004/0176353 A1 | 9/2004 | Oxford et al. | |
| 2004/0247628 A1 | 12/2004 | Lintz et al. | |
| 2005/0054655 A1 | 3/2005 | Beaulieu et al. | |
| 2005/0186276 A1 | 8/2005 | Berchielli et al. | |
| 2005/0261271 A1 | 11/2005 | Feng et al. | |
| 2007/0197489 A1 | 8/2007 | Karlsson et al. | |
| 2008/0003283 A1 | 1/2008 | Feng et al. | |
| 2008/0108807 A1 | 5/2008 | Feng et al. | |
| 2008/0108808 A1 | 5/2008 | Feng et al. | |
| 2008/0113993 A1 | 5/2008 | De Belin et al. | |
| 2008/0125437 A1 | 5/2008 | Dong et al. | |
| 2008/0142759 A1 | 6/2008 | Pays | |
| 2008/0161562 A1 | 7/2008 | Feng et al. | |
| 2008/0177064 A1 | 7/2008 | Feng et al. | |
| 2008/0188501 A1 | 8/2008 | Feng et al. | |
| 2008/0199410 A1 | 8/2008 | Johnson et al. | |
| 2008/0206163 A1 | 8/2008 | Oxford et al. | |
| 2008/0254127 A1 | 10/2008 | Watanabe et al. | |
| 2009/0012059 A1 | 1/2009 | Feng et al. | |
| 2009/0075939 A1 | 3/2009 | He et al. | |
| 2010/0113413 A1 | 5/2010 | Dong et al. | |

(Continued)

FOREIGN PATENT DOCUMENTS

| | | |
|---|---|---|
| AU | 527997 B2 | 3/1983 |
| DE | 28 47 693 A1 | 5/1980 |

(Continued)

OTHER PUBLICATIONS

Dose Ranging Study of RPL554 in Chronic Obstructive Pulmonary Disease (COPD) Patients, ClinicalTrials.gov, (2019). https://www.clinicaltrials.gov/study/NCT03443414.

Hankinson, et al., Spirometric reference values from a sample of the general U.S. population, Am J Respir Crit Care Med., 159(1):179-187, (1999).

Miller, et al., Standardisation of spirometry, Eur Respir J., 26(2):319-338, (2005).

Record History | ver. 42: Jul. 11, 2022 | NCT04535986 | ClinicalTrials.gov.

Record History | ver. 43: May 13, 2022 | NCT04542057 | ClinicalTrials.gov.

U.S. Appl. No. 18/825,447, filed Sep. 5, 2024.

(Continued)

*Primary Examiner* — Savitha M Rao
(74) *Attorney, Agent, or Firm* — Foley & Lardner LLP

(57) ABSTRACT

The disclosure relates to a particulate composition comprising ensifentrine, wherein the particulate composition further comprises: from greater than 0.00 wt % to 0.60 wt % of 1,3-bis(2-(2-(mesitylimino)-9,10-dimethoxy-4-oxo-6,7-dihydro-2H-pyrimido[6,1-a]isoquinolin-3(4H)-yl)ethyl)urea (BMIQU) relative to the total weight of ensifentrine; and from 0.00 wt % to 0.50 wt % of a biuret impurity of formula (A) relative to the total weight of ensifentrine. Further disclosed herein are liquid pharmaceutical compositions comprising the particulate composition, and a process for producing the particulate composition are also described.

26 Claims, No Drawings

(56) References Cited

U.S. PATENT DOCUMENTS

| | | |
|---|---|---|
| 2010/0204471 A1 | 8/2010 | Tomita |
| 2011/0076276 A1 | 3/2011 | Guo et al. |
| 2011/0190261 A1 | 8/2011 | Dong et al. |
| 2012/0251594 A1 | 10/2012 | Longest et al. |
| 2012/0302533 A1 | 11/2012 | Oxford et al. |
| 2013/0078256 A1 | 3/2013 | Guo et al. |
| 2013/0158021 A1 | 6/2013 | Dong et al. |
| 2013/0225616 A1 | 8/2013 | Walker et al. |
| 2014/0242174 A1 | 8/2014 | Walker |
| 2016/0000790 A1 | 1/2016 | Walker et al. |
| 2016/0008363 A1 | 1/2016 | Walker et al. |
| 2017/0112839 A1 | 4/2017 | Abbott-Banner et al. |
| 2017/0239178 A1 | 8/2017 | Spargo et al. |
| 2017/0266190 A1 | 9/2017 | Walker et al. |
| 2018/0021337 A1 | 1/2018 | Spargo et al. |
| 2018/0369139 A1 | 12/2018 | Spargo et al. |
| 2019/0330206 A1 | 10/2019 | Spargo |
| 2020/0016158 A1 | 1/2020 | Spargo et al. |
| 2021/0106585 A1 | 4/2021 | Abbott-Banner et al. |
| 2021/0379053 A1 | 12/2021 | Spargo et al. |
| 2022/0265549 A1 | 8/2022 | Spargo et al. |
| 2023/0112220 A1 | 4/2023 | Spargo et al. |
| 2024/0165023 A1 | 5/2024 | Spargo et al. |
| 2024/0165054 A1 | 5/2024 | Rheault et al. |
| 2024/0165055 A1 | 5/2024 | Rheault et al. |
| 2024/0165117 A1 | 5/2024 | Spargo et al. |
| 2024/0173327 A1 | 5/2024 | Rickard et al. |
| 2024/0382489 A1 | 11/2024 | Spargo et al. |
| 2025/0000866 A1 | 1/2025 | Spargo et al. |

FOREIGN PATENT DOCUMENTS

| | | |
|---|---|---|
| DE | 42 40 981 A1 | 6/1994 |
| DE | 19612194 A1 | 10/1997 |
| DE | 19820947 A1 | 11/1998 |
| DE | 19821263 A1 | 11/1998 |
| DE | 19726241 A1 | 12/1998 |
| EP | 0 601 401 A1 | 6/1994 |
| EP | 0 876 366 A2 | 11/1998 |
| EP | 0 983 334 A1 | 3/2000 |
| EP | 1 305 026 A2 | 5/2003 |
| EP | 1 418 896 A2 | 5/2004 |
| EP | 1 438 019 A1 | 7/2004 |
| EP | 1 519 711 A1 | 4/2005 |
| EP | 1 586 571 A1 | 10/2005 |
| EP | 1 651 611 A2 | 5/2006 |
| EP | 1 825 467 A2 | 8/2007 |
| EP | 1 892 269 A1 | 2/2008 |
| EP | 1 993 540 A2 | 11/2008 |
| EP | 2 063 903 A1 | 6/2009 |
| EP | 2 167 476 A2 | 3/2010 |
| JP | 2001-213867 A | 8/2001 |
| JP | 3675274 B2 | 7/2005 |
| JP | 2005-263780 A | 9/2005 |
| KR | 101361145 B1 | 2/2014 |
| WO | WO-97/26258 A1 | 7/1997 |
| WO | WO-97/36039 A1 | 10/1997 |
| WO | WO-98/45293 A1 | 10/1998 |
| WO | WO-98/51772 A1 | 11/1998 |
| WO | WO-99/01607 A2 | 1/1999 |
| WO | WO-00/58308 A1 | 10/2000 |
| WO | WO-00/58309 A1 | 10/2000 |
| WO | WO-01/93841 A2 | 12/2001 |
| WO | WO-02/17894 A2 | 3/2002 |
| WO | WO-03/000343 A2 | 1/2003 |
| WO | WO-03/035030 A1 | 5/2003 |
| WO | WO-03/037262 A2 | 5/2003 |
| WO | WO-2004/004684 A1 | 1/2004 |
| WO | WO-2005/007092 A2 | 1/2005 |
| WO | WO-2005/007138 A1 | 1/2005 |
| WO | WO-2005/021510 A2 | 3/2005 |
| WO | WO-2005/095381 A1 | 10/2005 |
| WO | WO-2006/061398 A2 | 6/2006 |
| WO | WO-2008/023249 A1 | 2/2008 |
| WO | WO-2008/036293 A1 | 3/2008 |
| WO | WO-2008/140553 A2 | 11/2008 |
| WO | WO-2009/005674 A2 | 1/2009 |
| WO | WO-2012/020016 A1 | 2/2012 |
| WO | WO-2012/037782 A1 | 3/2012 |
| WO | WO-2012/051426 A2 | 4/2012 |
| WO | WO-2013/034909 A1 | 3/2013 |
| WO | WO-2013/034910 A1 | 3/2013 |
| WO | WO-2013/063468 A1 | 5/2013 |
| WO | WO-2013/092791 A1 | 6/2013 |
| WO | WO-2013/118855 A1 | 8/2013 |
| WO | WO-2013/128283 A2 | 9/2013 |
| WO | WO-2014/037726 A1 | 3/2014 |
| WO | WO-2014/037727 A1 | 3/2014 |
| WO | WO-2014/140647 A1 | 9/2014 |
| WO | WO-2014/140648 A1 | 9/2014 |
| WO | WO-2015/173551 A1 | 11/2015 |
| WO | WO-2016/042313 A1 | 3/2016 |
| WO | WO-2016/128742 A1 | 8/2016 |
| WO | WO-2018/020249 A1 | 2/2018 |
| WO | WO-2020/074894 A1 | 4/2020 |
| WO | WO-2021/028679 A1 | 2/2021 |
| WO | WO-2021/150268 A1 | 7/2021 |
| WO | WO-2021/171034 A1 | 9/2021 |
| WO | WO-2022/261417 A1 | 12/2022 |
| WO | WO-2023/076205 A1 | 5/2023 |
| WO | WO-2023/156794 A1 | 8/2023 |
| WO | WO-2024/033624 A1 | 2/2024 |
| WO | WO-2024/033625 A1 | 2/2024 |
| WO | WO-2024/033626 A1 | 2/2024 |
| WO | WO-2024/033627 A1 | 2/2024 |
| WO | WO-2024/084212 A1 | 4/2024 |

OTHER PUBLICATIONS

U.S. Appl. No. 18/946,234, filed Nov. 13, 2024.

Abbott-Banner, K.H. et al., Dual PDE3/4 and PDE4 inhibitors: Novel treatments for COPD and other inflammatory airway diseases, Basic & Clinical Pharmacology & Toxicology, vol. 114, (2014):365-376.

Akers (Sterile Drug Products: Formulation, Packaging, Manufacture and Quality. Published 2010) (Year: 2010), 517 pages.

Albert, RK et al., Azithromycin for prevention of exacerbations of COPD. N. Engl. J. Med. 2011; 365(8):689-98.

Anzueto, A et al., Ensifentrine, a novel phosphodiesterase 3 and 4 inhibitor for the treatment of chronic obstructive pulmonary disease: randomized, double-blind, placebo-controlled, multicenter phase III trials (the Enhance Trials). Am J Respir Crit Care Med. 2023;208(4):406-416.

Anzueto, A. et al., Effect of Ensifentrine, a Novel PDE3 and PDE4 Inhibitor, on Lung Function, Symptoms and Exacerbations in Patients with COPD: The Enhance Trials (PowerPoint slides), ATS 2023, Washington DC May 19-24, 2023.

Anzueto, A. et al., Treatment with Ensifentrine, a Dual PDE3 and PDE4 Inhibitor, Significantly Reduced Exacerbation Rate and Risk in Subjects with COPD: Sub-group Results from the Phase 3 Trial, Enhance-2 (Poster at ATS 2023—May 19-24, 2023).

Anzueto, A. et al., Treatment with ensifentrine, a dual PDE3 and PDE4 inhibitor, significantly reduced exacerbation rate and risk in subjects with COPD: sub-group results from the phase 3 trial, enhance-2, Am J Respir Crit Care Med, (2023):207:A4998.

Anzueto, A., Impact of exacerbations on COPD. Eur. Respir. Rev. 2010;19(116):113-8.

Au, DH et al., The effects of smoking cessation on the risk of chronic obstructive pulmonary disease exacerbations. J Gen Intern Med. 2009;24(4):457-63.

Bafadhel, M et al., Predictors of exacerbation risk and response to budesonide in patients with chronic obstructive pulmonary disease: a post-hoc analysis of three randomised trials. Lancet Respir Med 2018; 6(2): 117-26.

Barjaktarevic, I. et al., Ensifentrine, a Novel Dual Phosphodiesterase (PDE) 3 and 4 Inhibitor, Significantly Reduces Annualized Exacerbations and Delays the Time to First Exacerbation in COPD: Pooled Sub-group Analyses of Enhance-1 and Enhance-2 Phase 3 Trials (Poster at ATS 2023—May 19-24, 2023).

(56) References Cited

OTHER PUBLICATIONS

Barjaktarevic, I. et al., Ensifentrine, a novel dual phosphodiesterase (PDE) 3 and 4 inhibitor, significantly reduces annualized exacerbations and delays the time to first exacerbation in COPD: pooled sub-group analyses of enhance-1 and enhance-2 phase 3 trials, Am J Respir Crit Care Med, (2023):207:A5008.
Bjermer, L. et al., Efficacy and safety of a first-in-class inhaled PDE3/4 inhibitor (ensifentrine) vs salbutamol in asthma, Pulmonary Pharmacology & Therapeutics, vol. 58, (2019).
Blasko, G. et al., Pyrimido[1,6-a]pyrido[3,4-b]indoles as new platelet inhibiting agents, European Journal of Medicinal Chemistry, vol. 21, 2 (1986):91-5.
Brat, K et al., Prognostic properties of the GOLD 2023 classification system. Int J Chron Obstruct Pulmon Dis. 2023;18:661-667.
Breo USPI 2013.
Cazzola et al., "Ensifentrine (RPL554): an investigational PDE3/4 inhibitor for the treatment of COPD," Expert Opinion on Investigational Drugs, Sep. 1, 2019, 28(10):827-833.
Cazzola, M. et al., Ensifentrine (RPL554): and inhaled 'bifunctional' dual PDE3/4 inhibitor for the treatment of asthma and chronic obstructive pulmonary disease, Pharmaceutical Patent Analyst, vol. 7, 6(2018):249-257.
Chen, E.H et al., Modifications of primaquine as antimalarials. 1. 5-Phenoxy derivatives of primaquine, Journal of Medicinal Chemistry, vol. 20, 8 (1977):1107-9.
Daliresp (roflumilast). Package insert. AstraZeneca; 2020.
Daliresp USPI 2011.
Developing innovative therapies for the treatment of respiratory diseases, Nov. 2023 (presentation from Verona website).
Dong-Sheng, M. et al., Synthesis of Daimuron, College of Chemistry and Chemical Engineering, Huaxue Yu Nianhe, vol. 6, (2003):293-295.
Dransfield, MT et al., Acute exacerbations and lung function loss in smokers with and without chronic obstructive pulmonary disease. Am J Respir Crit Care Med. 2017;195(3):324-330.
Duffy, SP et al., Chronic obstructive pulmonary disease: evaluation and management. Med Clin North Am. 2019;103(3):453-461.
Enhance-1 Phase 3 data—Dec. 2022 (presentation from Verona website).
Enhance-2 Phase 3 data—Aug. 2022 (presentation from Verona website).
Experimental report filed with response dated Dec. 13, 2021 to first office action on Chinese Application No. 202010090019.5, including translation of experimental report.
Experimental report filed with response dated Jan. 17, 2022 on Korean Patent Application No. 10-2017-7006862, including translation of experimental report.
Experimental report filed with response dated Jul. 4, 2022 to second office action on Chinese Application No. 202010090019.5, including translation of experimental report.
Ferguson, G.T. et al., A Dose-Ranging Study of the Novel Inhaled Dual PDE 3 and 4 Inhibitor Ensifentrine in Patients with COPD Receiving Maintenance Tiotropium Therapy, International Journal of Chronic Obstructive Pulmonary Disease, vol. 16, (2021):1137-1148, with Supplement to Manuscript, 32 pages.
Ferguson, G.T. et al., A Dose-Ranging Study of the Novel Inhaled Dual PDE 3 and 4 Inhibitor Ensifentrine in Patients with COPD Receiving Maintenance Tiotropium Therapy, International Journal of Chronic Obstructive Pulmonary Disease, vol. 16, (2021):1137-1148.
Franciosi, L.G. et al., Efficacy and safety of RPL554, a dual PDE3 and PDE4 inhibitor, in healthy volunteers and in patients with asthma or chronic obstructive pulmonary isease: findings from four clinical trials, The Lancet. Respiratory Medicine, vol. 1, 9(2013):714-727.
Frank, A.W., Synthesis of some carbonyl derivatives of tris(aminomethyl)phosphine oxide, Phosphorus and Sulfur and the Related Elements, vol. 22, 3(1985):265-76.
Global Initiative for Chronic Obstructive Lung Disease, 2021 Report, 2021, 54 pages.
Global strategy for the diagnosis, management, and prevention of chronic obstructive pulmonary disease 2022 report. Global Initiative for Chronic Obstructive Lung Disease (GOLD). Accessed Jun. 13, 2024. https://goldcopd.org/wp-content/uploads/2021/12/GOLD-REPORT-2022-v1.1-22Nov2021_WMV.pdf.
Global strategy for the diagnosis, management, and prevention of chronic obstructive pulmonary disease 2023 report. Global Initiative for Chronic Obstructive Lung Disease (GOLD).
Global strategy for the diagnosis, management, and prevention of chronic obstructive pulmonary disease 2024 report. Global Initiative for Chronic Obstructive Lung Disease (GOLD). Accessed Apr. 16, 2024. https://goldcopd.org/2024-gold-report/.
Harries, TH et al., Blood eosinophil count, a marker of inhaled corticosteroid effectiveness in preventing COPD exacerbations in post-hoc RCT and observational studies: systematic review and meta-analysis. Respir Res. Jan. 3, 2020;21(1):3.
Houlihan, W.J. et al., Synthesis and proton-NMR spectra, Journal of Heterocyclic Chemistry, vol. 19, 6(1982):1453-6.
Hurst, JR et al., Prognostic risk factors for moderate-to-severe exacerbations in patients with chronic obstructive pulmonary disease: a systematic literature review. Respir Res. 2022;23(1):213.
Iheanacho, I. et al., Economic burden of chronic obstructive pulmonary disease (COPD): a systematic literature review. Int J Chron Obstruct Pulmon Dis. 2020;15:439-460.
International Search Report on PCT/GB2023/052082 dated Oct. 20, 2023.
International Search Report on PCT/GB2023/052083 dated Oct. 31, 2023.
International Search Report on PCT/GB2023/052084 dated Oct. 23, 2023.
International Search Report on PCT/GB2023/052085 dated Nov. 15, 2023.
Jansen, M., Derivatives of some nuclear methoxylated B-phenylethylamines, vol. 50, (1931):617-37.
Kew, KM et al., Inhaled steroids and risk of pneumonia for chronic obstructive pulmonary disease. Cochrane Database Syst. Rev. 2014; 2014(3):Cd010115.
Kienzle, F. et al., Synthesis of 6,7-dihydro-2H-pyrimido[6,1-a]isoquinolin-4(3H)-ones and analogous compounds and their activity as blood platelet aggregation inhibitors, Helvetica Chimica Acta, vol. 69, 7(1986):1671-80.
Kijima, I, et al., Synthesis and reactivities of triisocyanatoantimony, Japan, Nippon Kagaku Kaishi, vol. 12, (1986):1754-57.
Labiris, N.R. et al., Pulmonary drug delivery. Part II: The role of inhalant delivery devices and drug formulations in therapeutic effectiveness of aerosolized medications, Br J Clin Pharmacol., vol. 56, (2003):600-612.
Lal, B. et al., Synthesis of 2-substituted-6,7-dihydro-4H-pyrimido[6, 1-a]thieno[2,3-c]- and [3,2-c]pyridin-4-ones, Heterocycles, vol. 24, 7(1986):1977-85.
Lal, B. et al., Trequinsin, a potent new antihypertensive vasodilator in the series of 2-(arylimino)-3-alkyl-9, 10-dimethoxy-3,4,6,7-tetrahydro-2H-pyrimido[6, 1-a]isoquinolin-4-ones, Journal of Medicinal Chemistry, vol. 27, 11(1984):1470-80.
Le Brun, P.P.H. et al., A review of the technical aspects of drug nebulization, Pharmacy World and Science, vol. 22, 3(2000):75-81.
Lipson, DA et al., Fulfil trial: once-daily triple therapy for patients with chronic obstructive pulmonary disease. Am J Respir Crit Care Med. 2017;196(4):438-446.
Lipson, DA et al., Once-daily single-inhaler triple versus dual therapy in patients with COPD. N Engl J Med. 2018; 378(18):1671-1680.
Mahler, DA et al., Effect of ensifentrine on dyspnea in patients with moderate-to-severe chronic obstructive pulmonary disease: pooled analysis of the Enhance trials. Expert Rev Respir Med. Aug. 2024;18(8):645-654. doi: 10.1080/17476348.2024.2389960. Epub Aug. 8, 2024. PMID: 39106052.
Mahler, DA et al., Ensifentrine, A Novel, Selective Inhibitor of PDE3 and PDE4, Improved Dyspnea in Subjects With Symptomatic, Moderate-to-Severe COPD Over 24 Weeks (Abstract and Poster), A27. Emerging Treatments and Therapeutic Strategies in COPD: Results of Clinical Trials and Observational Studies / Poster Discussion Session / Sunday May 19/09:15 AM / San Diego

(56) References Cited

OTHER PUBLICATIONS

Convention Center, Room 33A-C. American Journal of Respiratory and Critical Care Medicine 2024;209:A1205.

Mannich, C. et al., Berichte der Deutschen Chemischen Gesellschaft, vol. 43, (1910):189-97.

Mannino, D et al., Treatment patterns for chronic obstructive pulmonary disease (COPD) in the United States: results from an observational cross-sectional physician and patient survey. Int J Chron Obstruct Pulmon Dis. 2022;17:749-761.

Mantero, M. et al., Acute exacerbations of COPD: risk factors for failure and relapse, International Journal of COPD, vol. 12, (2017):2687-2693.

Martinez, FJ et al., Determinants of response to roflumilast in severe chronic obstructive pulmonary disease. Pooled analysis of two randomized trials. Am J Respir Crit Care Med. Nov. 15, 2018;198(10):1268-1278.

Matera, M.G. et al., Prospects for COPD treatment, Current Opinion In Pharmacology, vol. 56, (2021):74-84.

Maurer et al., "Late Breaking Abstract—RPL554, a first-in-class dual PDE3/4 inhibitor, causes significant bronchodilation and symptom relief; a Phase 2B Copd study," European Respiratory Journal, 2018, 52:OA1940, 1-5.

Milara, J et al., Oxidative stress-induced glucocorticoid resistance is prevented by dual PDE3/PDE4 inhibition in human alveolar macrophages. Clin Exp Allergy. 2011;41(4):535-46.

Miravitlles, M et al., A pooled analysis of mortality in patients with COPD receiving dual bronchodilation with and without additional inhaled corticosteroid. Int J Chron Obstruct Pulmon Dis. 2022;17:545-558.

Negewo et al., "Peripheral blood eosinophils: a surrogate marker for airway eosinophilia in stable COPD," International Journal of COPD, 2016, 11:1495-1504.

Nici, L et al., Pharmacologic management of chronic obstructive pulmonary disease. an official American Thoracic Society clinical practice guideline. Am J Respir Crit Care Med. 2020;201(9):e56-e69.

No Author, European Medicines Agency, Guideline on the sterilisation of the medicinal product, active substance, excipient and primary container, Apr. 11, 2016.

No Author, European Medicines Agency, Guideline on the sterilisation of the medicinal product, active substance, excipient and primary container, Mar. 6, 2019.

Pai, N.R. et al., Synthesis of novel analogs 3,4-dihydro-1H-quinolin-2-one derivatives as typical Antidepressant, Sedative and anti-Parkinson agents, Heterocyclic Letters, vol. 2, 1 (2012):117-128.

Pascoe, S et al., Blood eosinophils and treatment response with triple and dual combination therapy in chronic obstructive pulmonary disease: analysis of the Impact trial. Lancet Respir Med 2019;7:745-756.

Pasquale, MK et al., Impact of exacerbations on health care cost and resource utilization in chronic obstructive pulmonary disease patients with chronic bronchitis from a predominantly Medicare population. Int J Chron Obstruct Pulmon Dis. 2012; 7:757-64.

Pavord, ID et al., Blood eosinophil count and pneumonia risk in patients with chronic obstructive pulmonary disease: a patient-level meta-analysis. Lancet Respir Med. 2016;4(9):731-741.

Pfleiderer, V.W. et al., Synthesis of 9-substituted xanthines, Justus Liebigs Annalen der Chemie, vol. 631, (1960):168-74.

Preparing to launch the first novel MOA in COPD in 10 years, Oct. 18, 2023 (presentation from Verona website).

Rabe, KF et al., Anti-inflammatory effects of roflumilast in chronic obstructive pulmonary disease (Robert): a 16-week, randomised, placebo-controlled trial. Lancet Respir Med. Nov. 2018;6(11):827-836. doi: 10.1016/S2213-2600(18)30331-X. Epub Sep. 14, 2018. Erratum in: Lancet Respir Med. Oct. 12, 2018;: PMID: 30224319.

Rabe, KF et al., Triple inhaled therapy at two glucocorticoid doses in moderate-to-very-severe COPD. N Engl J Med. 2020; 383(1):35-48.

Ratel, M. et al., Imidazolium-Based Ionic Liquid Surfaces for Biosensing, Analytical Chemistry, vol. 85, 12 (2013):5770-5777.

Rheault, T. et al., Effect of ensifentrine on lung function and health-related quality of life (QoL) by COPD severity: analysis from a phase 2b dose ranging study, American Journal of Respiratory and Critical Care Medicine, (2021):203:A2254.

Roca, J. et al., References values for forced spirometry, Eur Respir J., vol. 11, (1998):1354-1362.

Rothnie, KJ et al., Natural history of chronic obstructive pulmonary disease exacerbations in a general practice-based population with chronic obstructive pulmonary disease. Am J Respir Crit Care Med. 2018;198(4):464-471.

Schmidt, DT et al., The effect of selective and non-selective phosphodiesterase inhibitors on allergen- and leukotriene C(4)-induced contractions in passively sensitized human airways. Br J Pharmacol. 2000;131(8):1607-18.

Sciurba, F.C. et al., Ensifentrine, a novel dual phosphodiesterase (PDE) 3 and 4 inhibitor, improves lung function, symptoms, quality of life and reduces exacerbation rate and risk in patients with COPD: results from replicate phase 3 trials, Am J Respir Crit Care Med, (2023):207, poster.

Sciurba, F.C. et al., Ensifentrine, a novel dual phosphodiesterase (PDE) 3 and 4 inhibitor, improves lung function, symptoms, quality of life and reduces exacerbation rate and risk in patients with COPD: results from replicate phase 3 trials, Am J Respir Crit Care Med, (2023):207:A5005.

Sciurba, FC et al., Dual Phosphodiesterase 3 and 4 Inhibitor Ensifentrine Reduces Exacerbation Rate and Risk in Patients With Moderate to Severe COPD. Chest. Aug. 27, 2024:S0012-3692(24)04937-7. doi: 10.1016/j.chest.2024.07.168. Epub ahead of print. PMID: 39197510.

Sciurba, FC et al., Ensifentrine, A Novel, Selective Inhibitor of PDE3 and PDE4, Reduced Moderate/Severe Exacerbation Rate and Risk in Subjects With COPD Regardless of Baseline Blood Eosinophils (Abstract and Poster), B52. Evidence for Therapeutic Strategies in COPD: From Established to Emerging/ Thematic Poster Session / Monday, May 20/09:15 AM-04:15 PM / San Diego Convention Center, Area F. American Journal of Respiratory and Critical Care Medicine 2024;209:A3820.

Singh et al., "Blood Eosinophil Counts in Chronic Obstructive Pulmonary Disease: A Biomarker of Inhaled Corticosteroid Effects," Tuberculosis and Respiratory Disease, 2020, 83:185-194.

Singh, D. et al., A dose-ranging study of the inhaled dual phosphodiesterase 3 and 4 inhibitor ensifentrine in COPD, Respiratory Research, vol. 21, (2020).

Singh, D. et al., Efficacy and safety of CHF6001, a novel inhaled PDE4 inhibitor in COPD: the Pioneer study, Respir Res., vol. 21, (2020):246.

Singh, D. et al., The short-term bronchodilator effects of the dual phosphodiesterase 3 and 4 inhibitor RPL554 in COPD, Eur Respir J., vol. 52, (2018):1801074.

Sonnex, K et al., Impact of smoking status on the efficacy of inhaled corticosteroids in chronic obstructive pulmonary disease: a systematic review. BMJ Open. 2020;10(4):e037509.

Span 20 (sorbitan monolaurate) Product Page, Sigma Aldrich, Published 2024 (Year: 2024), 8 pages.

Spiriva Respimat USPI (US product insert), 2014.

Suissa, S, Number needed to treat in COPD: exacerbations versus pneumonias. Thorax. 2013;68(6):540-3.

Suissa, Samy, Single-inhaler triple versus dual bronchodilator therapy for GOLD E and other exacerbating patients with COPD: Real-world comparative effectiveness and safety, European Respiratory Journal 2023.

Symbicort USPI 2006.

Tashkin DP, et al., Concomitant inhaled corticosteroid use and the risk of pneumonia in COPD: a matched-subgroup post hoc analysis of the UPLIFT trial. Respir Res. 2018; 19(1):196.

Taylor, N.P., Verona sets sights on Philb after CPOD drug comes through early trial, Fierce Biotech article, (2015).

Tran, P. et al., Structure-activity relationship of human glutaminyl cyclase inhibitors having an N-(5-methy-1H-imidazol-1-yl)propyl thiourea template, Bioorganic & Medicinal Chemistry, vol. 21, 13(2013):3821-3830.

Tudorza USPI 2012.

(56) References Cited

OTHER PUBLICATIONS

Turner, MJ et al., The dual phosphodiesterase 3 and 4 inhibitor RPL554 stimulates CFTR and ciliary beating in primary cultures of bronchial epithelia. Am J Physiol Lung Cell Mol Physiol. 2015;310(1):L59-70.
Tween 20 (polyoxyethylene sorbitan monolaurate) Product Page, Sigma Aldrich, Published 2024 (Year 2024), 9 pages.
USP 1229.8 Dry Heat Sterilization 2018.
Verona Pharma Announces Analyses Demonstrating Ensifentrine Reduced Exacerbation Rates Across Subgroups in Phase 3 Enhance-2 Trial for COPD, Oct. 14, 2022 (press release from Verona website).
Verona Pharma, Clinical Study Protocol, Version 5.0, Apr. 30, 2021 (Year: 2021).
Vogelmeier, CF et al., Evaluation of exacerbations and blood eosinophils in UK and US COPD populations. Respir Res. 2019;20(1):178.
Watz, H et al., Symptom improvement following treatment with the inhaled dual phosphodiesterase 3 and 4 inhibitor ensifentrine in patients with moderate to severe COPD—A Detailed Analysis. Int J Chron Obstruct Pulmon Dis. 2020;15:2199-2206.
Zafari, Z. et al., Projecting long-term health and economic burden of COPD in the United States. Chest. 2021; 159(4):1400-1410.
Zafari, Z. et al., The projected economic and health burden of sub-optimal asthma control in Canada. Respiratory Medicine. 2018; 138:7-12.
Zuo, H. et al., Phosphodiesterases as therapeutic targets for respiratory diseases, Pharmacology & Therapeutics, vol. 197, (2019):225-242.

PARTICULATE COMPOSITION

CROSS-REFERENCE

This application is a Continuation of U.S. application Ser. No. 18/753,759, filed Jun. 25, 2024, which claims the benefit of GB Application No. 2309605.0, filed Jun. 26, 2023, U.S. Provisional Application No. 63/550,786, filed Feb. 7, 2024, and U.S. Provisional Application No. 63/550,792, filed Feb. 7, 2024, each of which is incorporated herein by reference in its entirety.

FIELD OF THE DISCLOSURE

The present disclosure relates to a particulate composition comprising ensifentrine, as well as a pharmaceutical composition and a process for producing the particulate composition.

BACKGROUND OF THE DISCLOSURE

Ensifentrine (N-(2-{(2E)-9,10-dimethoxy-4-oxo-2-[(2,4,6-trimethylphenyl)imino]-6,7-dihydro-2H-pyrimido[6,1-a]isoquinolin-3(4H)-yl}ethyl)urea, also known as RPL554) is a dual PDE3/PDE4 inhibitor and is described in WO 00/58308 A1.

As a combined PDE3/PDE4 inhibitor, ensifentrine has both bronchodilatory and anti-inflammatory activity and is useful in the treatment of respiratory disorders including chronic obstructive pulmonary disease (COPD). The chemical structure of ensifentrine is shown below.

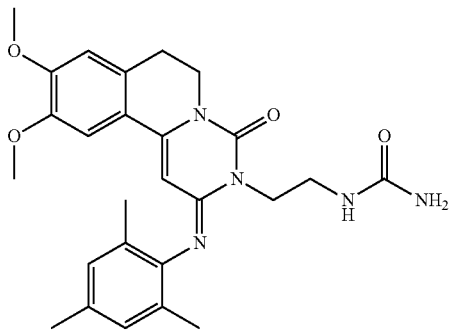 [SMILES: COc1cc2c(cc1OC)-c1c/c(=N\c3c(C)cc(C)cc3C)n(CCNC(N)=O)c(=O)n1CC2]

Impurities associated with active agents need to be controlled, with only certain levels of specific impurities permitted in pharmaceutical products (with these impurities in some cases referred to as related substances). It has been found that known processes for producing ensifentrine are associated with undesirable levels of impurities. For instance, the process described in WO 00/58308 A1 in which a urea group is added using sodium cyanate and aqueous hydrochloric produces an ensifentrine substance containing a biuret impurity which could not readily be removed. WO 2018/020249 A1 discusses several possible reagents which may be used to add a urea group in the final step of the production of ensifentrine, but no detailed discussion of the conditions of the final ureation step is provided.

It is desirable to develop a synthetic process for the production of ensifentrine which produces a drug substance with a favourable impurity profile without the need for extensive purification and recrystallisation, and in particular where the drug substance comprises low levels of a biuret impurity.

SUMMARY OF THE DISCLOSURE

It has been found that it is possible to produce ensifentrine with a favourable impurity profile, and in particular ensifentrine having low levels of a biuret impurity, by a reaction comprising reacting an amine intermediate with 4-nitrophenyl chloroformate and ammonia in a solvent comprising dichloromethane.

In some embodiments, the disclosure provides a particulate composition comprising ensifentrine, wherein the particulate composition further comprises:

from greater than 0.00 wt % to 0.60 wt % of 1,3-bis(2-(2-(mesitylimino)-9,10-dimethoxy-4-oxo-6,7-dihydro-2H-pyrimido[6,1-a]isoquinolin-3(4H)-yl)ethyl)urea (BMIQU) relative to the total weight of ensifentrine; and from 0.00 wt % to 0.50 wt % of a biuret impurity of formula (A) relative to the total weight of ensifentrine:

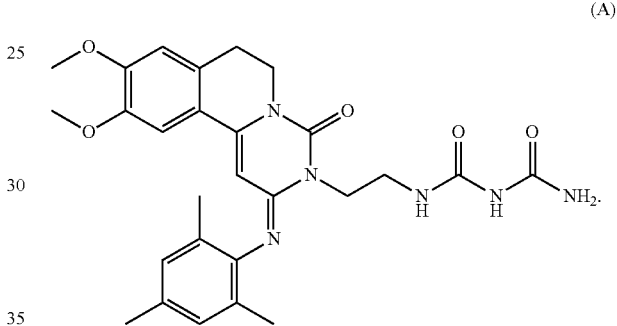

(A)

In some embodiments, the particulate composition comprises the biuret impurity.

In some embodiments, the disclosure also provides a liquid pharmaceutical composition suitable for administration by inhalation comprising (a) the particulate composition disclosed herein and (b) a diluent.

Further provided by the disclosure is a process for producing the particulate composition. In some embodiments, the process comprising: reacting a compound of formula (IV) with 4-nitrophenyl chloroformate and ammonia, wherein the compound of formula (IV), 4-nitrophenyl chloroformate and ammonia are reacted in a solvent comprising dichloromethane,

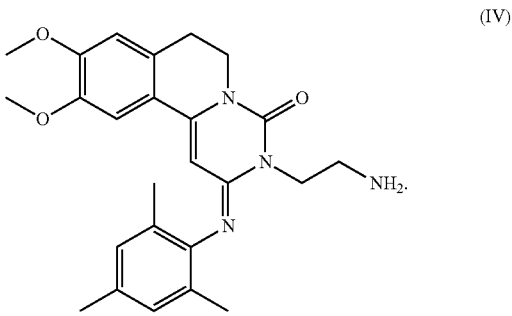 [SMILES: COc1cc2c(cc1OC)-c1c/c(=N\c3c(C)cc(C)cc3C)n(CCN)c(=O)n1CC2]

(IV)

Further provided herein, in some embodiments, are liquid pharmaceutical compositions, wherein the liquid pharmaceutical composition is a suspension comprising, relative to the total weight of the liquid pharmaceutical composition: (a) 1.2 mg/mL ensifentrine; (b) 0.5 mg/ml polysorbate 20; (c) 0.05 mg/ml sorbitan monolaurate; (d) 0.744 mg/ml sodium dihydrogen phosphate; (e) 0.853 mg/ml disodium hydrogen phosphate; (f) 8.6 mg/ml sodium chloride; and (g) water.

Further provided herein, in some embodiments, is a method of (a) treating moderate chronic obstructive pulmonary disease (COPD); (b) treating severe COPD; (c) increasing trough lung function; or (d) reducing frequency of an exacerbation of COPD; in a human subject in need thereof, the method comprising administering to the human subject via inhalation the particulate composition or liquid pharmaceutical composition provided herein.

In some embodiments, provided herein is a kit comprising the particulate composition provided herein or the liquid pharmaceutical composition provided herein.

DETAILED DESCRIPTION OF THE DISCLOSURE

Certain Definitions

As used herein and in the appended claims, the singular forms "a," "and," and "the" include plural referents unless the context clearly dictates otherwise. Thus, for example, reference to "an agent" includes a plurality of such agents. When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range may vary between 1% and 10% of the stated number or numerical range.

The term "comprising" (and related terms such as "comprise" or "comprises" or "having" or "including") is not intended to exclude. An embodiment of any composition of matter, composition, method, or process, or the like, described herein, may "consist of" or "consist essentially of" the described features.

As used herein, unless stated otherwise, "%" or "percent" as used herein means percent by weight (e.g., w/w %), percent by volume (e.g., v/v %), molar percentage (e.g., mol/mol %). Preferably, "%" or "percent" as used herein means percent by weight (e.g., w/w %).

The terms "treat," "treating," or "treatment" as used herein, include reducing, alleviating, abating, ameliorating, managing, relieving, or lessening the symptoms associated with a disease, disease state, condition, or indication (e.g., provided herein) in either a chronic or acute therapeutic scenario. Also, treatment of a disease or disease state described herein includes the disclosure of use of such compound or composition for the treatment of such disease, disease state, disorder, or indication.

Particulate Composition

The disclosure provides a particulate composition comprising ensifentrine. In some embodiments, the particulate composition is formed of particles comprising ensifentrine. The particulate composition may be a powder comprising particles of ensifentrine. The particulate composition may be present in combination with a separate medium. For instance, the particulate composition may be in the form of a powder comprising ensifentrine, which powder is dispersed in a diluent or which powder is combined with a second particulate composition (for instance a second particulate composition comprising a carrier such a lactose).

In some instances, the particulate compositions comprise no more than about 0.5 wt % (e.g., no more than about 0.45 wt %, 0.4 wt %, 0.36 wt %, 0.3 wt %, 0.25 wt %, 0.2 wt %, 0.15 wt %, or 0.1 wt %) of other related substances (e.g., substances other than ensifentrine). In some instances, the particulate compositions comprise at least about 0.01 wt % (e.g., at least about 0.02 wt %, 0.04 wt %, 0.08 wt %, 0.1 wt %, 0.12 wt %, 0.14 wt %, 0.18 wt %, 0.2 wt %, 0.25 wt %, 0.3 wt %, 0.35 wt %, 0.4 wt %, 0.45 wt %, or 0.5 wt %) of other related substances (e.g., substances other than ensifentrine). In some embodiments, the particulate compositions comprise from about 0 wt % to about 0.5 wt %, about 0.01 wt % to about 0.4 wt %, about 0.01 wt % to about 0.3 wt %, about 0.05 wt % to about 0.5 wt %, about 0.1 wt % to about 0.5 wt %, or about 0.1 wt % to about 0.4 wt % of other related substances (e.g., substances other than ensifentrine). In some embodiments, particulate compositions comprise about 0.01 wt %, 0.05 wt %, 0.1 wt %, 0.15 wt %, 0.2 wt %, 0.25 wt %, 0.3 wt %, 0.35 wt %, 0.4 wt %, 0.45 wt %, or about 0.5 wt % of other related substances (e.g., substances other than ensifentrine).

In some embodiments, in addition to ensifentrine, a particulate composition disclosed herein further comprises: from greater than 0.00 wt % to 0.60 wt % of 1,3-bis(2-(2-(mesitylimino)-9,10-dimethoxy-4-oxo-6,7-dihydro-2H-pyrimido[6,1-a]isoquinolin-3(4H)-yl)ethyl)urea (BMIQU) relative to the total weight of ensifentrine; and from 0.00 wt % to 0.50 wt % of a biuret impurity of formula (A) relative to the total weight of ensifentrine:

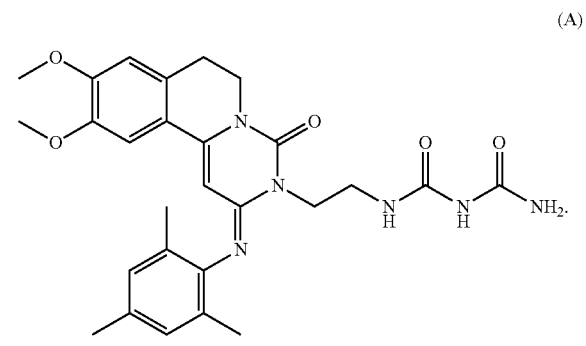 [SMILES: COc1cc2c(cc1OC)-c1c/c(=N\c3c(C)cc(C)cc3C)n(CCNC(=O)NC(N)=O)c(=O)n1CC2]

(A)

In some instances, the particulate compositions comprise a biuret impurity. In some embodiments, the biuret impurity comprises of formula (A). In some embodiments, the particulate compositions comprise from about 0 wt % to about 0.5 wt % of the biuret impurity of formula (A). In some embodiments, the particulate compositions comprise at least 0.01 wt % (e.g., at least 0.01 wt %, 0.02 wt %, 0.03 wt %, 0.04 wt % 0.05 wt %, 0.1 wt %, 0.15 wt %, 0.2 wt %, 0.25 wt %, 0.3 wt %, 0.35 wt %, 0.4 wt %, 0.5 wt %) of the biuret impurity of formula (A). In some embodiments, the particulate compositions comprise at most 1 wt % (e.g., at most 0.9 wt %, 0.8 wt %, 0.7 wt %, 0.65 wt %, 0.6 wt %, 0.55 wt %, 0.5 wt %, or 0.4 wt %) of the biuret impurity of formula (A). In some embodiments, the particulate compositions comprise from about 0 wt % to about 1 wt %, 0 wt % to about 0.04 wt %, about 0.01 wt % to about 0.5 wt %, 0.02 wt % to about 0.5 wt %, 0.05 wt % to about 0.5 wt %, 0.05 wt % to about 0.6 wt %, 0.05 wt % to about 0.8 wt %, 0.05 wt % to about 1.0 wt %, or about 0.1 wt % to about 0.5 wt % of the biuret impurity of formula (A). In some embodiments, the particulate compositions comprise from about 0.01 wt % to about 0.1 wt % of the biuret impurity of formula (A). In some embodiments, the particulate compositions comprise about 0 wt %, 0.01 wt %, 0.02 wt %, 0.03 wt %, 0.04 wt % 0.05 wt %, 0.07 wt %, 0.1 wt %, 0.15 wt %, 0.2 wt %, 0.25 wt %, 0.3 wt %, 0.35 wt %, 0.4 wt %, 0.5 wt %, 0.6 wt %, 0.7 wt %, 0.8 wt %, 0.9 wt % or 1 wt % of the biuret impurity of formula (A).

In some embodiments, the weight percentage is relative to the total weight of ensifentrine in the particulate composition. In some embodiments, BMIQU and, if present, the biuret impurity are present in the particles comprising ensifentrine in the particulate composition. The content of BMIQU, the biuret impurity and other related substances or impurities may be as measured by high performance liquid chromatography (HPLC).

In some embodiments, the particulate composition may comprise from 0.00 wt % to 0.30 wt % of the biuret impurity relative to the total weight of ensifentrine. In some embodiments, the particulate composition may comprises from 0.00 wt % to 0.05 wt % of the biuret impurity relative to the total weight of ensifentrine. The particulate composition may, for instance, comprise from 0.00 wt % to 0.03 wt % of the biuret impurity relative to the total weight of ensifentrine. The particulate composition may comprise at least 0.005 wt % BMIQU relative to the total weight of ensifentrine. The particulate composition may comprise from 0.01 wt % to 0.30 wt % of BMIQU relative to the total weight of ensifentrine. The particulate composition may comprise from 0.30 wt % to 0.60 wt % of BMIQU relative to the total weight of ensifentrine. The particulate composition may comprise from 0.02 wt % to 0.06 wt % of BMIQU relative to the total weight of ensifentrine. The structure of BMIQU is shown below.

In some embodiments, the particulate composition comprises at least 0.01 wt % (e.g., at least 0.02 wt %, 0.04 wt %, 0.06 wt %, 0.1 wt %, 0.12 wt %, 0.15 wt %, 0.17 wt %, 0.2 wt %, 0.25 wt %, or 0.3 wt %) of BMIQU (e.g., relative to the total weight of ensifentrine). In some embodiments, the particulate composition comprises at most 0.5 wt % (e.g., at most 0.45 wt %, 0.4 wt %, 0.35 wt %, 0.3 wt %, 0.25 wt %, or 0.2 wt %) of BMIQU. In some embodiments, the particulate composition comprises from about 0 wt % to about 1 wt %, 0 wt % to about 0.5 wt %, about 0 wt % to about 0.4 wt %, about 0 wt % to about 0.3 wt %, about 0.01 wt % to about 0.3 wt %, about 0.01 wt % to about 0.2 wt %, 0.02 wt % to about 0.1 wt %, or about 0.01 wt % to about 0.1 wt %. In some embodiments, the particulate composition comprises about 0 wt %, 0.01 wt %, 0.02 wt %, 0.05 wt %, 0.07 wt %, 0.1 wt %, 0.15 wt %, 0.2 wt %, 0.25 wt %, or 0.3 wt % BMIQU. In some instances, the wt % is relative to the total weight of ensifentrine.

In some embodiments, the particulate composition optionally further comprises 1-(2-(9-hydroxy-2-(mesitylimino)-10-methoxy-4-oxo-6,7-dihydro-2H-pyrimido[6,1-a]isoquinolin-3(4H)-yl)ethyl)urea (9-des-methyl impurity) and/or 1-(2-(10-hydroxy-2-(mesitylimino)-9-methoxy-4-oxo-6,7-dihydro-2H-pyrimido[6,1-a]isoquinolin-3(4H)-yl)ethyl)urea (10-des-methyl impurity). The structures of these compounds are shown below.

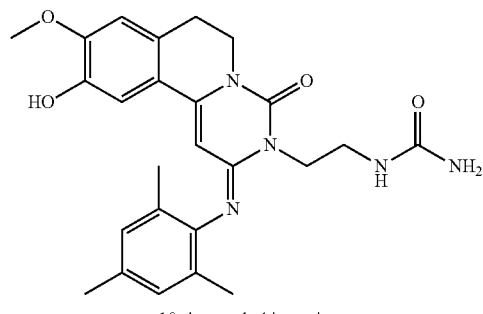

10-des-methyl impurity

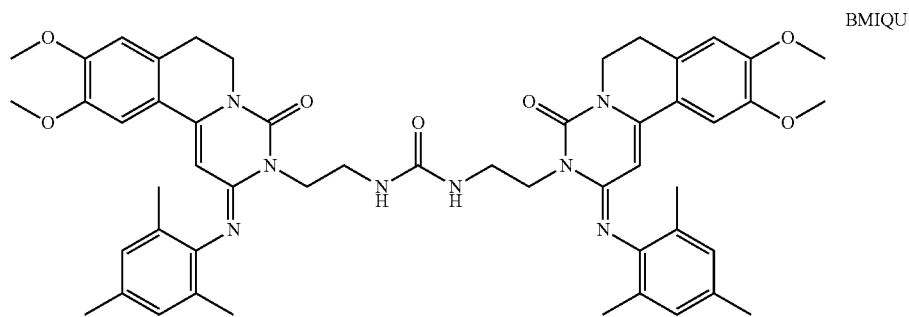

BMIQU

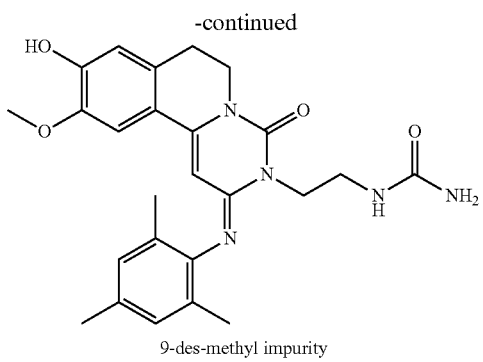

9-des-methyl impurity

In some embodiments, the particulate composition may further comprise: from greater than 0.00 wt % to 0.10 wt % of the 9-des-methyl impurity; and/or from greater than 0.00 wt % to 0.10 wt % of the 10-des-methyl impurity, relative to the total weight of ensifentrine. The particulate composition may further comprise from 0.01 wt % to 0.10 wt % of the 9-des-methyl impurity and from greater than 0.01 wt % to 0.10 wt % of the 10-des-methyl impurity, relative to the total weight of ensifentrine.

In some instances, the particulate composition further comprises the 9-des-methyl impurity. In some embodiments, the particulate composition comprises from about 0 to about 0.1 wt % of the 9-des-methyl impurity. In some embodiments, the particulate composition comprises at least 0.01 wt % (e.g., at least 0.02 wt %, 0.03 wt %, 0.04 wt %, 0.05 wt %, 0.06 wt %, 0.07 wt %, 0.08 wt %, 0.09 wt %, 0.1 wt %, 0.15 wt %, or 0.2 wt %) of the 9-des-methyl impurity. In some embodiments, the particulate composition comprises at most 0.3 wt % (e.g., at most 0.28 wt %, 0.26 wt %, 0.24 wt %, 0.22 wt %, 0.2 wt %, 0.18 wt %, 0.15 wt %, or 0.1 wt %) the 9-des-methyl impurity. In some embodiments, the particulate composition comprises from about 0.01 wt % to about 0.3 wt %, 0.01 wt % to about 0.25 wt %, 0.01 wt % to about 0.2 wt %, 0.05 wt % to about 0.2 wt %, 0.01 wt % to about 0.1 wt %, or from about 0.1 wt % to about 0.2 wt % of the 9-des-methyl impurity. In some embodiments, the particulate composition comprises about 0 wt %, 0.01 wt %, 0.04 wt %, 0.06 wt %, 0.1 wt %, 0.12 wt %, 0.14 wt %, 0.16 wt %, 0.18 wt %, 0.2 wt %, 0.24 wt %, 0.28 wt %, or about 0.3 wt % of the 9-des-methyl impurity. In some embodiments, the particulate composition comprise less than about 1 wt % of the 9-des-methyl impurity.

In some instances, the particulate composition further comprises the 10-des-methyl impurity. In some embodiments, the particulate composition comprises from about 0 to about 0.1 wt % of the 10-des-methyl impurity. In some embodiments, the particulate composition comprises at least 0.01 wt % (e.g., at least 0.02 wt %, 0.03 wt %, 0.04 wt %, 0.05 wt %, 0.06 wt %, 0.07 wt %, 0.08 wt %, 0.09 wt %, 0.1 wt %, 0.15 wt %, or 0.2 wt %) of the 10-des-methyl impurity. In some embodiments, the particulate composition comprises at most 0.3 wt % (e.g., at most 0.28 wt %, 0.26 wt %, 0.24 wt %, 0.22 wt %, 0.2 wt %, 0.18 wt %, 0.15 wt %, or 0.1 wt %) the 10-des-methyl impurity. In some embodiments, the particulate composition comprises from about 0.01 wt % to about 0.3 wt %, 0.01 wt % to about 0.25 wt %, 0.01 wt % to about 0.2 wt %, 0.01 wt % to about 0.1 wt %, 0.05 wt % to about 0.2 wt %, or from about 0.1 wt % to about 0.2 wt % of the 10-des-methyl impurity. In some embodiments, the particulate composition comprises about 0 wt %, 0.01 wt %, 0.04 wt %, 0.06 wt %, 0.1 wt %, 0.12 wt %, 0.14 wt %, 0.16 wt %, 0.18 wt %, 0.2 wt %, 0.24 wt %, 0.28 wt %, or about 0.3 wt % of the 10-des-methyl impurity. In some embodiments, the particulate composition comprise less than about 1 wt % of the 10-des-methyl impurity. For example, the particulate composition may comprise: from 0.01 to 0.04 wt % of 10-des-methyl impurity; from 0.05 to 0.09 wt % of the 9-des-methyl impurity; from 0.01 to 0.03 wt % of the biuret impurity; and from 0.02 to 0.06 wt % of BMIQU, wherein the wt % is relative to the total weight of ensifentrine in the particulate composition. In some embodiments, the particulate composition may comprise: from 0.01 to 0.4 wt % of 10-des-methyl impurity; from 0.05 to 0.9 wt % of the 9-des-methyl impurity; from 0.01 to 0.5 wt % of the biuret impurity; and from 0.02 to 0.6 wt % of BMIQU, wherein the wt % is relative to the total weight of ensifentrine in the particulate composition.

In some embodiments, the particulate composition may further comprise (E)-2-(mesitylimino)-9,10-dimethoxy-2,3,6,7-tetrahydro-4H-pyrimido[6,1-a]isoquinolin-4-one (compound (1)) and/or (E)-3-(2-aminoethyl)-2-(mesitylimino)-9,10-dimethoxy-2,3,6,7-tetrahydro-4H-pyrimido[6,1-a]isoquinolin-4-one (compound (IV)), the structures of which are shown below. In some embodiments, the particulate composition may comprise neither compound (1) nor compound (IV), or the particulate composition comprises less than 0.04 wt % total of compound (1) and compound (IV) relative to the total weight of ensifentrine.

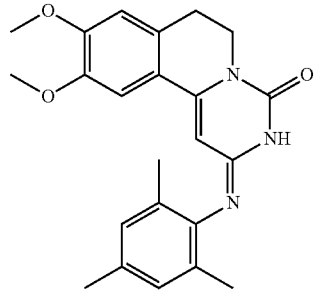

compound (I)

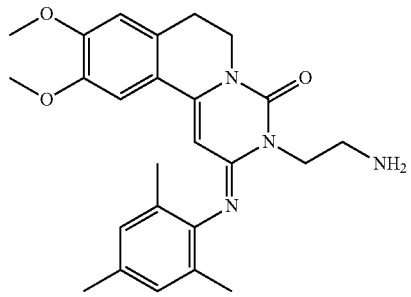

compound (IV)

In some instances, the particulate composition comprises compound (I). In some embodiments, the particulate composition comprises from about 0 to about 0.1 wt % of compound (1). In some embodiments, the particulate composition comprises at least 0.01 wt % (e.g., at least 0.02 wt %, 0.03 wt %, 0.04 wt %, 0.05 wt %, 0.06 wt %, 0.07 wt %, 0.08 wt %, 0.09 wt %, 0.1 wt %, 0.15 wt %, or 0.2 wt %) of compound (1). In some embodiments, the particulate composition comprises at most 0.3 wt % (e.g., at most 0.28 wt %, 0.26 wt %, 0.24 wt %, 0.22 wt %, 0.2 wt %, 0.18 wt %, 0.15 wt %, or 0.1 wt %) compound (1). In some embodiments, the particulate composition comprises from about 0.01 wt % to about 0.3 wt %, 0.01 wt % to about 0.25 wt %, 0.01 wt % to about 0.2 wt %, 0.01 wt % to about 0.1 wt %, 0.05 wt % to about 0.2 wt %, or from about 0.1 wt % to about 0.2 wt % of compound (1). In some embodiments, the particulate composition comprises about 0 wt %, 0.01 wt %, 0.04 wt %, 0.06 wt %, 0.1 wt %, 0.12 wt %, 0.14 wt %, 0.16 wt %, 0.18 wt %, 0.2 wt %, 0.24 wt %, 0.28 wt %, or about 0.3 wt % of compound (1). In some embodiments, the particulate composition comprises less than about 1 wt % of compound (1).

In some instances, the particulate composition comprises compound (IV). In some embodiments, the particulate composition comprises from about 0 to about 0.1 wt % of compound (IV). In some embodiments, the particulate composition comprises at least 0.01 wt % (e.g., at least 0.02 wt %, 0.03 wt %, 0.04 wt %, 0.05 wt %, 0.06 wt %, 0.07 wt %, 0.08 wt %, 0.09 wt %, 0.1 wt %, 0.15 wt %, or 0.2 wt %) of compound (IV). In some embodiments, the particulate composition comprises at most 0.3 wt % (e.g., at most 0.28 wt %, 0.26 wt %, 0.24 wt %, 0.22 wt %, 0.2 wt %, 0.18 wt %, 0.15 wt %, or 0.1 wt %) compound (IV). In some embodiments, the particulate composition comprises from about 0.01 wt % to about 0.3 wt %, 0.01 wt % to about 0.25 wt %, 0.01 wt % to about 0.2 wt %, 0.01 wt % to about 0.1 wt %, 0.05 wt % to about 0.2 wt %, or from about 0.1 wt % to about 0.2 wt % of compound (IV). In some embodiments, the particulate composition comprises about 0 wt %, 0.01 wt %, 0.04 wt %, 0.06 wt %, 0.1 wt %, 0.12 wt %, 0.14 wt %, 0.16 wt %, 0.18 wt %, 0.2 wt %, 0.24 wt %, 0.28 wt %, or about 0.3 wt % of compound (IV). In some embodiments, the particulate composition comprises less than about 1 wt % of compound (IV).

In some embodiments, one or more of the compounds BMIQU, biuret impurity, 9-des-methyl impurity, 10-des-methyl impurity, compound (1) and compound (IV), if present, may optionally be present in the form of salts. In some embodiments, BMIQU, biuret impurity, 9-des-methyl impurity, 10-des-methyl impurity, compound (I) and compound (IV) are present in free base form.

In some embodiments, the particulate composition comprises less than 15000 ppm (e.g., less than 10000 ppm, 5000 ppm, or 2500 ppm) of residual organic solvents. In some embodiments, the particulate composition comprises from 100 ppm to 15000 ppm (e.g., from 500 ppm to 15000 ppm, from 1000 ppm to 15000 ppm, from 1000 ppm to 10000 ppm, or from 5000 ppm to 15000 ppm) of residual organic solvents.

In some embodiments, the residual organic solvent is an organic solvent leftover from the methods of preparing ensifentrine. In some embodiments, the residual organic solvent is selected from acetone, acetonitrile, dichloromethane, methanol, toluene, tetrahydrofuran, dimethyl sulfoxide, or a combination thereof. In some embodiments, the residual organic solvent comprises a combination of acetone, acetonitrile, dichloromethane, methanol, toluene, tetrahydrofuran, and dimethyl sulfoxide, such as in amounts described herein.

In some embodiments, the amount of residual organic solvent is determined from gas chromatography.

In some embodiments, the residual organic solvent is acetone. In some embodiments, the acetone is present in the particulate composition in an amount of less than 5000 ppm (e.g., less than 3500 ppm, 3000 ppm, 2500 ppm, 2000 ppm, 1500 ppm, or 1000 ppm). In some embodiments, the acetone is present in the particulate composition in an amount of from about 100 ppm to 5000 ppm (e.g., from 500 ppm to 5000 ppm, from 1000 ppm to 5000 ppm, or from 500 ppm to 4000 ppm).

In some embodiments, the residual organic solvent is acetonitrile. In some embodiments, the acetonitrile is present in the particulate composition in an amount of less than 410 ppm (e.g., less than 400 ppm, 350 ppm, 300 ppm, 250 ppm, 200 ppm, 150 ppm, or 100 ppm). In some embodiments, the acetonitrile is present in the particulate composition in an amount of from 100 ppm to 410 ppm (e.g., from 100 ppm to 350 ppm, from 200 ppm to 410 ppm, or from 300 ppm to 400 ppm).

In some embodiments, the residual organic solvent is dichloromethane. In some embodiments, the dichloromethane is present in the particulate composition in an amount of less than 5000 ppm (e.g., less than 3500 ppm, 3000 ppm, 2500 ppm, 2000 ppm, 1500 ppm, or 1000 ppm). In some embodiments, the dichloromethane is present in the particulate composition in an amount of from about 100 ppm to 5000 ppm (e.g., from 500 ppm to 5000 ppm, from 1000 ppm to 5000 ppm, or from 500 ppm to 4000 ppm).

In some embodiments, the residual organic solvent is methanol. In some embodiments, the methanol is present in the particulate composition at an amount of less than 3000 ppm (e.g., less than 2500 ppm, 2000 ppm, 1500 ppm, 1000 ppm, or 500 ppm). In some embodiments, the methanol is present in the particulate composition at an amount of from 500 ppm to 3000 ppm (e.g., 1000 ppm to 3000 ppm, 1500 ppm to 3000 ppm, or from 2000 ppm to 3000 ppm).

In some embodiments, the residual organic solvent is toluene. In some embodiments, the toluene is present in the particulate composition in an amount of less than 5000 ppm (e.g., less than 3500 ppm, 3000 ppm, 2500 ppm, 2000 ppm, 1500 ppm, or 1000 ppm). In some embodiments, the toluene is present in the particulate composition in an amount of from about 100 ppm to 5000 ppm (e.g., from 500 ppm to 5000 ppm, from 1000 ppm to 5000 ppm, or from 500 ppm to 4000 ppm).

In some embodiments, the residual organic solvent is tetrahydrofuran. In some embodiments, the tetrahydrofuran is present in the particulate composition in an amount of less than 720 ppm (e.g., less than 700 ppm, 650 ppm, 600 ppm, 550 ppm, 500 ppm, 450 ppm, or 400 ppm). In some embodiments, the tetrahydrofuran is present in the particulate composition in an amount of from 250 ppm to 720 ppm (e.g., from 400 ppm to 720 ppm, from 500 ppm to 720 ppm, or from 600 ppm to 720 ppm).

In some embodiments, the residual organic solvent is dimethyl sulfoxide. In some embodiments, the dimethyl sulfoxide is present in the particulate composition in an amount of less than 5000 ppm (e.g., less than 3500 ppm, 3000 ppm, 2500 ppm, 2000 ppm, 1500 ppm, or 1000 ppm). In some embodiments, the dimethyl sulfoxide is present in the particulate composition in an amount of from about 100 ppm to 5000 ppm (e.g., from 500 ppm to 5000 ppm, from 1000 ppm to 5000 ppm, or from 500 ppm to 4000 ppm).

In some embodiments, the particulate composition comprises less than 5000 ppm acetone, less than 410 ppm acetonitrile, less than 5000 ppm dichloromethane, less than 3000 ppm methanol, less than less than 5000 pp toluene, less than 720 ppm tetrahydrofuran, and less than 5000 ppm dimethyl sulfoxide.

In some embodiments, the particulate compositions comprise one or more elemental impurities. In some embodiments, the elemental impurities are selected from nickel, arsenic, lead, cadmium, mercury, lithium, or any combination thereof.

In some embodiments, the elemental impurity is nickel. In some embodiments, the nickel is present in the particulate composition at an about of less than 200 ppm (e.g., less than 175 ppm, 150 ppm, 125 ppm, or 100 ppm).

In some embodiments, the elemental impurity is arsenic. In some embodiments, the arsenic is present in the particulate composition in an amount of less than 0.2 ppm (e.g., less than 0.17 ppm, 0.15 ppm, 0.13 ppm, 0.1 ppm, or less than 0.05 ppm).

In some embodiments, the elemental impurity is lead. In some embodiments, the lead is present in the particulate compositions in an amount of less than 0.5 ppm (e.g., less than 0.4 ppm, 0.3 ppm, 0.25 ppm, 0.2 ppm, 0.1 ppm, or 0.05 ppm).

In some embodiments, the elemental impurity is cadmium. In some embodiments, the cadmium is present in the particulate composition in an amount of less than 0.2 ppm (e.g., less than 0.17 ppm, 0.15 ppm, 0.13 ppm, 0.1 ppm, or less than 0.05 ppm).

In some embodiments, the elemental impurity is mercury. In some embodiments, the mercury is present in the particulate composition in an amount of less than 0.1 ppm (e.g., less than 0.08 ppm, 0.06 ppm, 0.05 ppm, 0.04 ppm, or 0.02 ppm).

In some embodiments, the elemental impurity is lithium. In some embodiments, the lithium is present in the particulate composition at an about of less than 200 ppm (e.g., less than 175 ppm, 150 ppm, 125 ppm, or 100 ppm).

In some embodiments, the particulate composition comprises less than 200 ppm nickel, less than 0.2 ppm arsenic, less than 0.5 ppm lead, less than 0.2 ppm cadmium, less than 0.1 ppm mercury, and less than 200 ppm lithium.

In some embodiments, the particulate composition may comprise at least 98.0 wt % of ensifentrine relative to the total weight of the particulate composition. The particulate composition may comprise at least 99.0 wt % of ensifentrine relative to the total weight of the particulate composition, or at least 99.2 wt % of ensifentrine relative to the total weight of the particulate composition. In some embodiments, the particulate compositions comprise at least 98 wt % (e.g., at least 98.5 wt %, 98.9 wt %, 99 wt %, 99.2 wt %, 99.4 wt %, 99.6 wt %, 99.8 wt %, or 99.9 wt %) of ensifentrine relative to the total weight of the particulate composition. In some embodiments, the particulate compositions comprise from about 95 wt % to about 99.9 wt %, about 96 wt % to about 99.9 wt %, about 97 wt % to about 99.5 wt %, 97 wt % to about 99 wt %, or about 98 wt % to about 99.9 wt % of ensifentrine relative to the total weight of the particulate composition. In some embodiments, the ensifentrine in the particulate composition is ensifentrine free base. In an alternative embodiment, the particulate composition comprises a pharmaceutically acceptable salt of ensifentrine.

In some embodiments, the ensifentrine is in crystalline form. Of the ensifentrine present in the particulate composition, at least 90 wt % may be in the form of ensifentrine free base Form 1. Ensifentrine free base Form I is a crystalline polymorph of ensifentrine (crystalline polymorph Form I) which in some embodiments has a powder X-ray diffraction pattern comprising characteristic peaks at 10.1° and 12.9°±0.1° 2θ. As stated herein, values of ° 2θ may be measured using an X-ray wavelength of CuKα radiation (λ=1.5406 Å). The powder X-ray diffraction pattern of Form I may further comprise characteristics peaks at 15.3° and 17.6°±0.1° 2θ. Form I of ensifentrine may have an powder X-ray diffraction pattern comprising at least 5 characteristic peaks selected from 6.4°, 10.1°, 12.6°, 12.9°, 13.6°, 14.2°, 14.7°, 15.3°, 15.4°, 15.8°, 17.0°, 17.6°, 18.9°, 20.9°, 22.4°, 22.8° and 28.7°±0.1° 2θ. Crystalline polymorph Form I may have a differential scanning calorimetry trace showing a maximum at 248° C.

The particulate composition may comprise at least 98.0 wt % or at least 99.0 wt % of ensifentrine crystalline polymorph Form I relative to the total weight of the particulate composition. In some embodiments, the particulate compositions comprise at least 98 wt % (e.g., at least 98.5 wt %, 98.9 wt %, 99 wt %, 99.2 wt %, 99.4 wt %, 99.6 wt %, 99.8 wt %, or 99.9 wt %) of ensifentrine crystalline polymorph Form I relative to the total weight of the particulate composition. In some embodiments, the particulate compositions comprise from about 95 wt % to about 99.9 wt %, about 96 wt % to about 99.9 wt %, about 97 wt % to about 99.5 wt %, 97 wt % to about 99 wt %, or about 98 wt % to about 99.9 wt % of ensifentrine crystalline polymorph Form I relative to the total weight of the particulate composition.

In some embodiments, the particulate composition comprises:
from 99.4 to 99.9 wt % of ensifentrine;
from 0.01 wt % to 0.30 wt % of BMIQU;
from 0.00 wt % to 0.10 wt % of the biuret impurity;
from 0.01 wt % to 0.20 wt % of the 9-des-methyl impurity; and
from 0.01 wt % to 0.20 wt % of the 10-des-methyl impurity,
wherein the wt % is relative to the total weight of the particulate composition.

The particulate composition may comprise:
from 99.5 to 99.9 wt % of ensifentrine;
from 0.02 wt % to 0.10 wt % of BMIQU;
from 0.00 wt % to 0.04 wt % of the biuret impurity;
from 0.01 wt % to 0.10 wt % of the 9-des-methyl impurity; and
from 0.01 wt % to 0.10 wt % of the 10-des-methyl impurity,
wherein the wt % is relative to the total weight of the particulate composition.

In some embodiments, the particulate composition may consist of:
from 99.6 to 99.9 wt % of ensifentrine;
from 0.02 wt % to 0.10 wt % of BMIQU;
from 0.00 wt % to 0.04 wt % of the biuret impurity;
from 0.01 wt % to 0.10 wt % of the 9-des-methyl impurity;
from 0.01 wt % to 0.10 wt % of the 10-des-methyl impurity; and
no greater than 0.36 wt % total of other related substances,
wherein the wt % is relative to the total weight of the particulate composition.

The particulate composition may comprise particles comprising ensifentrine and the additional impurity compounds defined above. The particulate composition may comprise particles of respirable size.

The particulate composition may have a Dv50 of from about 0.2 to about 5.0 μm. The particulate composition may have a Dv50 of from about 1.0 μm to about 2.2 μm. The particulate composition may have a Dv50 of at least 0.1 μm (e.g., at least 0.2 μm, 0.3 μm, 0.5 μm, 0.8 μm, 1 μm, 1.3 μm, 1.5 μm, 1.8 μm, 2 μm, 2.2 μm, 2.5 μm, 3 μm, 3.5 μm, or 4 μm). The particulate composition may have a Dv50 of at most 6 μm (e.g., at most 5.8 μm, 5.5 μm, 5.3 μm, 5.2 μm, 5.1 μm, 5 μm, or 4.5 μm).

The particulate composition may have a Dv10 of from about 0.2 μm to about 1 μm. The particulate composition may have a Dv10 of at least 0.1 μm (e.g., 0.15 μm, 0.18 μm, 0.2 μm, 0.4 μm, 0.6 μm, 0.8 μm, or 1 μm). The particulate composition may have a Dv10 of at most 1.3 μm (e.g., at most 1.2 μm, 1.1 μm, 1 μm, 0.95 μm, or 0.9 μm).

The particulate composition may have a Dv90 of at least 1.7 μm (e.g., at least 1.8 μm, 1.9 μm, 2 μm, 2.1 μm, 2.2 μm, 2.3 μm, or 2.4 μm). The particulate composition may have a Dv90 of at most 5.5 μm (e.g., at most 5.4 μm, 5.2 μm, 5 μm, 4.8 μm, 4.6 μm, 4.5 μm, or 4.4 μm).

The particulate composition may have a Dv10 of from about 0.3 μm to about 0.9 μm and/or a Dv90 of from about 2.3 μm to about 4.5 μm. The particulate composition may have a Dv50 of from about 1.0 μm to about 2.2 μm, a Dv10 of from about 0.3 μm to about 0.9 μm, and a Dv90 of from about 2.3 μm to about 4.5 μm The technique used to measure the Dv50 (and Dv10 and Dv90) values as stated herein may be laser diffraction. The particle size distribution of the particulate composition may be as measured by laser diffraction using a wet powder dispersion system. For instance, the particle size distribution can be measured by laser diffraction using a Malvern Spraytec in conjunction with a wet dispersion cell. In some embodiments, the instrument parameters for the Malvern Spraytec are as follows:
  particle—standard opaque particle;
  refractive index Particle—1.50;
  refractive index (imaginary)—0.50;
  density of particle—1.00;
  refractive index of dispersant—1.33;
  controller unit—1000 RPM;
  measurement type—timed;
  initial sampling time—30 s;
  obscuration—20%-30%;
  dispersant—1% Polysorbate 20 in deionised water.

The particulate composition may be produced by any pharmaceutically acceptable size reduction process or particle size controlled production process. For instance, the particles may be produced by size reduction of a solid form of ensifentrine, for example by air jet milling, mechanical micronisation or media milling, or by precipitation from a solution of ensifentrine. The disclosure also provides a solid form of ensifentrine having a composition as described for the particulate composition above (i.e. comprising ensifentrine and one or more of the stated impurity compounds), which solid form is in the form of a filter cake, a pellet, a block, a layer or a crystal.

Pharmaceutical Composition

The disclosure also provides a pharmaceutical composition comprising the particulate composition. The pharmaceutical composition may be a dry powder suitable for administration comprising the particulate composition and a carrier. The carrier may for instance be lactose powder.

In some embodiments, the pharmaceutical composition is a liquid pharmaceutical composition suitable for administration by inhalation comprising (a) the particulate composition and (b) a diluent. The particulate composition is in some instances suspended in the diluent.

The pharmaceutical composition may comprise any of the related substances (e.g., substances other than ensifentrine) described hereinabove and in the amounts described hereinabove. In some embodiments, the related substances comprise BMIQU, the biuret impurity of formula (A), the 9-des-methyl impurity, and the 10-des-methyl impurity.

The pharmaceutical composition may comprise no more than 1.00 wt % of BMIQU relative to the total weight of ensifentrine in the pharmaceutical composition. For instance, the liquid pharmaceutical composition may comprise no more than 0.50 wt % or no more than 0.20 wt % of BMIQU relative to the total weight of ensifentrine.

The pharmaceutical composition may comprise no more than 0.10 wt %, or no more than 0.05 wt %, of the biuret impurity relative to the total weight of ensifentrine in the pharmaceutical composition. In some embodiments, the pharmaceutical compositions provided herein further comprise one or more tonicity adjusters, one or more buffers, and one or more surfactants. In some embodiments, the pharmaceutical composition further comprises one or more tonicity adjusters. In some embodiments, the pharmaceutical composition further comprises one or more buffers. In some embodiments, the pharmaceutical composition further comprises one or more surfactants.

In some embodiments, the pharmaceutical compositions provided herein further comprise one or more tonicity adjusters. In some embodiments, the tonicity adjuster comprises sodium chloride. In some embodiments, the tonicity adjuster (e.g., sodium chloride) is present in the pharmaceutical composition at a concentration of at least 1 mg/mL (e.g., 2 mg/mL, 3 mg/mL, 4 mg/mL, 5 mg/mL, 6 mg/mL, 7 mg/mL). In some embodiments, the tonicity adjuster (e.g., sodium chloride) is present in the pharmaceutical composition at a concentration of at most 15 mg/mL (e.g., 14 mg/mL, 13 mg/mL, 12 mg/mL, 11 mg/mL, 10 mg/mL, 9 mg/mL). In some embodiments, the tonicity adjuster (e.g., sodium chloride) is present in the pharmaceutical composition at a concentration of from about 1 mg/mL to about 15 mg/mL, about 3 mg/mL to about 10 mg/mL, about 4 mg/mL to about 10 mg/mL, about 5 mg/mL to about 11 mg/mL, about 5 mg/mL to about 9 mg/mL, or about 6 mg/mL to about 9 mg/mL. In some embodiments, the tonicity adjuster (e.g., sodium chloride) is present in the pharmaceutical composition at a concentration of about 7 mg/mL to about 10 mg/mL. In some embodiments, the tonicity adjuster (e.g., sodium chloride) is present in the pharmaceutical composition at a concentration of 8 mg/mL to 9 mg/mL. In certain embodiments, the tonicity adjuster (e.g., sodium chloride) is present in the pharmaceutical composition at a concentration of (e.g., about) 8.6 mg/mL.

In some embodiments, the pharmaceutical compositions provided herein further comprise one or more buffers. In some embodiments, the buffer (e.g., sodium dihydrogen phosphate dihydrate and/or disodium hydrogen phosphate dihydrate) is present in the pharmaceutical composition at a concentration of at least 0.1 mg/mL (e.g., 0.2 mg/mL, 0.4 mg/mL, 0.8 mg/mL, 1 mg/mL, or 1.4 mg/mL). In some embodiments, the buffer (e.g., sodium dihydrogen phosphate dihydrate and/or disodium hydrogen phosphate dihydrate) is present in the pharmaceutical composition at a concentration of 4 mg/mL (e.g., 3.8 mg/mL, 3.3 mg/mL, 2.8 mg/mL, 2.5 mg/mL, or 2 mg/mL). In some embodiments, the buffer (e.g., sodium dihydrogen phosphate dihydrate and/or disodium hydrogen phosphate dihydrate) is present in the pharmaceutical composition at a concentration of about 1 mg/mL to about 2 mg/mL, about 1.2 mg/mL to about 1.8 mg/mL, or about 1.4 mg/mL to about 1.7 mg/mL. In some embodiments, the buffer (e.g., sodium dihydrogen phosphate dihydrate and/or disodium hydrogen phosphate dihydrate) is present in the pharmaceutical composition at a concentration of about 1.5 mg/mL to about 1.7 mg/mL.

In some embodiments, the pharmaceutical composition comprises sodium dihydrogen phosphate dihydrate at a concentration of at least 0.1 mg/mL (e.g., 0.2 mg/mL, 0.3 mg/mL, 0.4 mg/mL, 0.5 mg/mL, 0.6 mg/mL). In some embodiments, the pharmaceutical composition comprises sodium dihydrogen phosphate dihydrate at a concentration of at most 1.2 mg/mL (e.g., 1.1 mg/mL, 1.0 mg/mL, 0.9 mg/mL, 0.8 mg/mL). In some embodiments, the pharmaceutical composition comprises sodium dihydrogen phosphate dihydrate at a concentration of from about 0.5 mg/mL to about 0.9 mg/mL. In some embodiments, the pharmaceutical composition comprises sodium dihydrogen phosphate dihydrate at a concentration of about 0.7 mg/mL to about 0.8 mg/mL. In some embodiments, the pharmaceutical composition comprises sodium dihydrogen phosphate dihydrate at a concentration of about 0.7 mg/mL. In certain embodiments, the pharmaceutical composition comprises sodium dihydrogen phosphate dihydrate at a concentration of (e.g., about) 0.744 mg/mL.

In some embodiments, the pharmaceutical composition comprises disodium hydrogen phosphate dihydrate at a concentration of at least 0.1 mg/mL (e.g., 0.2 mg/mL, 0.3 mg/mL, 0.4 mg/mL, 0.5 mg/mL, 0.6 mg/mL, 0.7 mg/mL). In some embodiments, the pharmaceutical composition comprises disodium hydrogen phosphate dihydrate at a concentration of at most 1.2 mg/mL (e.g., 1.1 mg/mL, 1.0 mg/mL, 0.9 mg/mL). In some embodiments, the pharmaceutical composition comprises disodium hydrogen phosphate dihydrate at a concentration of from about 0.7 mg/mL to about 1 mg/mL. In some embodiments, the pharmaceutical composition comprises disodium hydrogen phosphate dihydrate at a concentration of about 0.8 mg/mL to about 0.9 mg/mL. In some embodiments, the pharmaceutical composition comprises disodium hydrogen phosphate dihydrate at a concentration of about 0.8 mg/mL. In some embodiments, the pharmaceutical composition comprises disodium hydrogen phosphate dihydrate at a concentration of about 0.9 mg/mL. In certain embodiments, the pharmaceutical composition comprises disodium hydrogen phosphate dihydrate at a concentration of (e.g., about) 0.853 mg/mL.

In some embodiments, the pharmaceutical composition comprises the one or more surfactants (e.g., polysorbate 20 and/or sorbitan monolaurate) in a concentration of at least 0.05 mg/mL (e.g., 0.1 mg/mL, 0.2 mg/mL, 0.3 mg/mL, 0.4 mg/mL). In some embodiments, the pharmaceutical composition comprises the one or more surfactants (e.g., polysorbate 20 and/or sorbitan monolaurate) in a concentration of at most 1 mg/mL (e.g., 0.9 mg/mL, 0.8 mg/mL, 0.7 mg/mL, 0.6 mg/mL). In some embodiments, the pharmaceutical composition comprises the one or more surfactants (e.g., polysorbate 20 and/or sorbitan monolaurate) in a concentration of from about 0.3 mg/mL to about 0.7 mg/mL. In some embodiments, the pharmaceutical composition comprises the one or more surfactants (e.g., polysorbate 20 and/or sorbitan monolaurate) at a concentration of from about 0.01 mg/mL to 2 mg/mL. In some embodiments, the pharmaceutical composition comprises the one or more surfactants (e.g., polysorbate 20 and/or sorbitan monolaurate) in a concentration of from about 0.4 mg/mL to about 0.6 mg/mL. In some embodiments, the pharmaceutical composition comprises the one or more surfactants (e.g., polysorbate 20 and/or sorbitan monolaurate) at a concentration of about 0.5 mg/mL. In some embodiments, the pharmaceutical composition comprises the one or more surfactants (e.g., polysorbate 20 and/or sorbitan monolaurate) at a concentration of about 0.6 mg/mL. In certain embodiments, the pharmaceutical composition comprises the one or more surfactants (e.g., polysorbate 20 and/or sorbitan monolaurate) in a concentration of (e.g., about) 0.55 mg/mL.

In some embodiments, the pharmaceutical composition comprises polysorbate 20 (e.g., Tween 20) in a concentration of at least 0.1 mg/mL (e.g., 0.2 mg/mL, 0.3 mg/mL, 0.4 mg/mL). In some embodiments, the pharmaceutical composition comprises polysorbate 20 (e.g., Tween 20) in a concentration of at most 1 mg/mL (e.g., 0.9 mg/mL, 0.8 mg/mL, 0.7 mg/mL, 0.6 mg/mL). In some embodiments, the pharmaceutical composition comprises polysorbate 20 (e.g., Tween 20) in a concentration of from about 0.3 mg/mL to about 0.7 mg/mL. In some embodiments, the pharmaceutical composition comprises polysorbate 20 (e.g., Tween 20) in a concentration of about 0.4 mg/mL to about 0.6 mg/mL. In certain embodiments, the pharmaceutical composition comprises polysorbate 20 (e.g., Tween 20) in a concentration of about 0.5 mg/mL.

In some embodiments, the pharmaceutical composition comprises sorbitan monolaurate (Span 20) in a concentration of at least 0.01 mg/mL (e.g., 0.02 mg/mL, 0.03 mg/mL, 0.04 mg/mL). In some embodiments, the pharmaceutical composition comprises sorbitan monolaurate (Span 20) in a concentration of at most 0.1 mg/mL (e.g., 0.09 mg/mL, 0.08 mg/mL, 0.07 mg/mL, 0.06 mg/mL). In some embodiments, the pharmaceutical composition comprises sorbitan monolaurate (Span 20) in a concentration of from about 0.03 mg/mL to about 0.07 mg/mL. In some embodiments, the pharmaceutical composition comprises sorbitan monolaurate (Span 20) in a concentration of from about 0.04 mg/mL to about 0.06 mg/mL. In certain embodiments, the pharmaceutical composition comprises sorbitan monolaurate (Span 20) in a concentration of (e.g., about) 0.05 mg/mL.

The liquid pharmaceutical composition may comprise, relative to the total weight of the liquid pharmaceutical composition: (i) the particulate composition at a concentration of from 0.8 to 1.6 mg/mL; (ii) one or more surfactants at a total concentration of from 0.1 to 1.0 mg/mL; (iii) one or more buffers at a total concentration of from 1.0 to 2.0 mg/ml; and (iv) water. The liquid pharmaceutical composition optionally further comprises a tonicity adjuster, which may have a concentration of from 1.0 to 20.0 mg/mL, or from 7.0 to 10.0 mg/mL. The tonicity adjuster may be sodium chloride.

The liquid pharmaceutical composition may comprise, relative to the total weight of the liquid pharmaceutical composition: (i) the particulate composition at a concentration of from 1.0 to 1.4 mg/mL, which particulate composition has a Dv50 of from about 1.0 µm to about 2.2 µm and optionally has a Dv10 of from about 0.3 µm to about 0.9 µm and a Dv90 of from about 2.3 µm to about 4.5 µm; (ii) one or more surfactants at a total concentration of from 0.4 to 0.7 mg/mL; (iii) one or more buffers at a total concentration of from 1.4 to 1.8 mg/ml; (iv) water; and (v) a tonicity adjuster at a concentration from 7.0 to 10.0 mg/mL. The liquid pharmaceutical composition may comprise at least 95 wt % or at least 99 wt % of (i), (ii), (iii), (iv) and optionally (v) relative to the total weight of the liquid pharmaceutical composition.

Examples of buffers include a citrate buffer, a phosphate buffer, an acetate buffer, and a bicarbonate buffer. Preferably, the one or more buffers comprise a phosphate buffer, for instance sodium dihydrogen phosphate dihydrate and/or disodium phosphate dihydrate.

Examples of surfactants include lecithin, oleic acid, polyoxyethylene glycol alkyl ethers (for instance PEG 300, PEG 600, PEG 1000, Brij 30, Brij 35, Brij 56, Brij 76 and Brij 97), polypropylene glycol (for instance PPG 2000), glucoside alkyl ethers, polyoxyethylene glycol octylphenol ethers, polyoxyethylene glycol alkylphenol ethers, glycerol alkyl esters, polyoxyethylene glycol sorbitan alkyl esters (polysorbates, for instance polysorbate 20, polysorbate 40, polysorbate 60 and polysorbate 80), sorbitan alkyl esters (for instance sorbitan monolaurate (Span 20), sorbitan monooleate (Span 80) and sorbitan trioleate (Span 85)), cocamide MEA, cocamide DEA, dodecyldimethylamine oxide, block copolymers of polyethylene glycol and polypropylene glycol (poloxamers), block copolymers of polyethylene glycol and polypropylene oxide (for instance Pluronic surfactants), polyvinyl pyrrolidone K25, polyvinyl alcohol, oligolactic acid, sodium dioctyl sulfosuccinate and polyethoxylated tallow amine (POEA).

Preferably, the one or more surfactants comprise a polysorbate and/or a sorbitan alkyl ester. The one or more surfactants may for instance comprise polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate) or polysorbate 80 (polyoxyethylene (20) sorbitan monooleate). The one or more surfactants may for instance comprise sorbitan monolaurate (Span 20), sorbitan monooleate (Span 80) or sorbitan trioleate (Span 85). Preferably, the one or more buffers comprise polysorbate 20 (Tween 20) and/or sorbitan monolaurate (Span 20).

The liquid pharmaceutical composition may comprise, relative to the total weight of the liquid pharmaceutical composition: (i) the particulate composition at a concentration of from 1.0 to 1.4 mg/mL, which particulate composition have a Dv50 of from about 1.0 µm to about 2.2 µm and optionally have a Dv10 of from about 0.3 µm to about 0.9 µm and a Dv90 of from about 2.3 µm to about 4.5 µm; (ii) one or more surfactants at a total concentration of from 0.4 to 0.7 mg/mL, which one or more surfactants are selected from a polysorbate and/or a sorbitan alkyl ester; (iii) one or more buffers at a total concentration of from 1.4 to 1.8 mg/mL, which one or more buffers are selected from phosphate buffers; (iv) water; and (v) sodium chloride at a concentration from 7.0 to 10.0 mg/mL.

The liquid pharmaceutical composition may for example comprise, relative to the total weight of the liquid pharmaceutical composition:
the particulate composition at a concentration of from 1.0 to 1.4 mg/mL;
polysorbate 20 (Tween 20) at a concentration of 0.3 to 0.7 mg/mL;
sorbitan monolaurate (Span 20) at a concentration of 0.0 to 0.1 mg/mL;
sodium dihydrogen phosphate dihydrate at a concentration of 0.5 to 1.0 mg/mL;
disodium hydrogen phosphate dihydrate at a concentration of 0.5 to 1.0 mg/mL;
sodium chloride at a concentration of 5 to 10 mg/mL; and
water.

The liquid pharmaceutical composition may comprise from about 2.0 mg to about 4.0 mg of the particulate composition. As such, the liquid pharmaceutical composition may comprise from about 2.0 mg to about 4.0 mg of ensifentrine.

In some embodiments, the liquid pharmaceutical composition is sterile. In specific embodiments, the liquid pharmaceutical compositions are sterile according to USP <71>.

The liquid pharmaceutical composition may have a sterility assurance level (SAL) of less than or equal to $10^{-3}$, less than or equal to $10^{-6}$, or less than or equal to $10^{-9}$. For instance, an SAL of $10^{-6}$ means that the probability that a final product is non-sterile is $1/10^6$. The sterile liquid pharmaceutical composition may have a total bioburden limit of less than or equal to 10 CFU/mL, or less than or equal to 1 CFU/mL. "CFU" is a colony forming unit. The bioburden may be as measured using a plate count method as described in USP 31 <61>, for instance the pour-plate method.

Typically, the sterility of the liquid pharmaceutical composition is as determined in accordance with USP <71> or Ph Eur 2.6.1. The liquid pharmaceutical composition typically meets the acceptance criteria as defined in USP <71> or Ph Eur 2.6.1.

In some embodiments, the liquid pharmaceutical compositions are stored in an ampule.

In some embodiments, the liquid pharmaceutical composition stored in an ampule is evaluated for leachates after 18 months at 25° C./60% RH (relative humidity), 6 months at 40° C./75% RH, or 33 months at 25° C./60% RH. In some embodiments, the liquid pharmaceutical compositions comprise elemental impurities below the ICH Q3D thresholds for daily exposure and do not increase during storage.

In some embodiments, the liquid pharmaceutical composition comprises 3,3-dimethyl-1,5-dioxacycloundecane-6,11-dione and 1,4,7-trioxacyclotridecane-8,13-dione in an amount less than the ICH M7 guideline threshold of toxicological concern. In some embodiments, the liquid pharmaceutical composition comprises 3,3-dimethyl-1,5-dioxacycloundecane-6,11-dione in an amount of less than the ICH M7 guideline threshold of toxicological concern. In some embodiments, the liquid pharmaceutical composition comprises 1,4,7-trioxacyclotridecane-8,13-dione in an amount of less than the ICH M7 guideline threshold of toxicological concern.

Also provided herein is a nebulizer comprising the liquid pharmaceutical composition. Nebulizer may be a soft mist nebulizer, a vibrating mesh nebulizer, a jet nebulizer and an ultrasonic wave nebulizer. In some embodiments, the nebulizer is a jet nebulizer.

In some embodiments, provided herein are kits comprising the particulate compositions provided herein. In other embodiments, the kits comprise the liquid pharmaceutical compositions provided herein.

In some embodiments, the kits comprise instructions for using any of the particulate compositions or liquid pharmaceutical compositions provided herein.

Methods of Treatment

In some embodiments, the liquid pharmaceutical composition disclosed herein may be for use in the treatment or prevention of a disease or condition selected from chronic obstructive pulmonary disease (COPD), asthma, allergic asthma, hay fever, allergic rhinitis, bronchitis, emphysema, bronchiectasis, adult respiratory distress syndrome (ARDS), steroid resistant asthma, severe asthma, paediatric asthma, cystic fibrosis, lung fibrosis, pulmonary fibrosis, interstitial lung disease, a skin disorder, atopic dermatitis, psoriasis, ocular inflammation, cerebral ischaemia, an inflammatory disease and an auto-immune disease. The disease or condition may be COPD or asthma. Often, the disease or condition is chronic obstructive pulmonary disease (COPD).

COPD

In some instances, the (e.g., liquid) pharmaceutical compositions may be used in methods of treating COPD. In some instances, the COPD is moderate COPD. In some instances, the COPD is severe COPD.

The above stages of COPD can be classified as set out below, where $FEV_1$ is forced expiratory volume in 1 second and FVC is forced vital capacity.
Mild COPD: $FEV_1/FVC<0.7$ and $FEV_1 \geq 80\%$ predicted
Moderate COPD: $FEV_1/FVC<0.7$ and $50\% \leq FEV_1<80\%$ predicted
Severe COPD: $FEV_1/FVC<0.7$ and $30\% \leq FEV_1<50\%$ predicted
Very Severe COPD: $FEV_1/FVC<0.7$ and $FEV_1<30\%$ predicted In each case the actual $FEV_1$ for the human subject is compared with a predicted $FEV_1$ value based on factors such as age and height of the human subject. These predicted values are readily available to the skilled person, for instance from the National Health and Nutrition Examination Survey III (Hankinson J L, Odencrantz J R, Fedan K B. Spirometry reference values from a sample of the general U.S. Population. Am J Respir Crit Care. 1999; 159:179-187). Examples of equations for calculating the predicted $FEV_1$ (in L) for a human subject are as follows, where H is height (cm) and A is age (yrs):

Males: 0.0430H—0.0290 A—2.490
Females: 0.0395H—0.025 A—2.600

The $FEV_1$ and FVC used to determine the severity of COPD in a human subject are measured by carrying out spirometry shortly after the administration of an adequate dose of at least one short-acting inhaled bronchodilator. In some embodiments, measurement of $FEV_1$ and FVC for determining COPD disease severity is done between 15 and 30 minutes following administration of salbutamol (albuterol).

In some embodiments, as used herein, $FEV_1$ and FVC are determined as set out in the article Standardisation of spirometry, Eur J 2005; 26; 319-338.

A human subject may have been determined to have moderate COPD by measuring $FEV_1/FVC<0.7$ and 50% s $FEV_1<80\%$ predicted $FEV_1$ value, where $FEV_1$ is forced expiratory volume in 1 second and FVC is forced vital capacity as measured between 15 and 30 minutes after a dose of a bronchodilator, optionally wherein the bronchodilator is salbutamol. A human subject may have been determined to have severe COPD by measuring $FEV_1/FVC<0.7$ and 30% s $FEV_1<50\%$ predicted, where $FEV_1$ is forced expiratory volume in 1 second and FVC is forced vital capacity as measured between 15 and 30 minutes after a dose of a bronchodilator, optionally wherein the bronchodilator is salbutamol. The determination of the human subject's COPD severity may take place at least 1 day prior to the first administration of the composition. In some embodiments, treatment with the composition disclosed herein increases average $FEV_1$ at least about 75, 90, or 100 mL in 12 weeks following administration.

Trough Lung Function

In some instances, the (e.g., liquid) pharmaceutical compositions may be used in methods of increasing trough lung function. An increase in trough lung function in a patient suffering from COPD is in some instances determined by measuring in increase in trough $FEV_1$, i.e. the $FEV_1$ of the patient shortly before administration of the composition as part of the maintenance therapy. In some embodiments, trough lung function is increased by at least 30 mL (e.g., at least 35 mL, 40 mL, 45 mL, 50 mL, or 55 mL). In some instances, the increase is measured after a certain period of time following a prior administration of the liquid pharmaceutical composition compared to the $FEV_1$ of the human subject prior to a first administration of the liquid pharmaceutical composition. In some embodiments, the period of time is about 11.5 to about 12 hours.

In some instances, the (e.g., liquid) pharmaceutical compositions may be used to increase morning trough lung function. Morning trough lung function can be measured by determining the $FEV_1$ of the patient shortly before the morning administration of the composition as part of the maintenance therapy. For instance, $FEV_1$ may be measured less than an hour before the morning administration of the composition. Morning trough $FEV_1$ may be the $FEV_1$ as measured between 11.5 and 12 hours following the prior evening dose.

COPD Exacerbations

In some instances the (e.g., liquid) pharmaceutical compositions may be used in methods of decreasing the frequency and/or severity of COPD exacerbations. In some embodiments, the COPD exacerbations are decreased by at least 30% (e.g., at least 32%, 34%, 36%, 40%, 45%, or 50%) compared to the frequency of the COPD exacerbation in an untreated subject and not administered the pharmaceutical composition disclosed herein.

In some embodiments, the methods comprise increasing the time to a first COPD exacerbation in the human subject. Accordingly, a subject may not have yet experienced a COPD exacerbation and the pharmaceutical composition disclosed herein may increase the time until the subject experiences a first COPD exacerbation (the first COPD exacerbation is delayed). The pharmaceutical composition may accordingly reduce the risk of COPD exacerbations in a COPD patient. The COPD exacerbations may comprise one or more of dyspnea (breathlessness), increased coughing, increased sputum volume, sputum purulence, wheezing, sore throat, a cold, and fever. Sputum purulence is a change in the colour of spontaneously expectorated samples from uncoloured to yellow-green. The COPD exacerbation may last for at least one day or at least two days.

A COPD exacerbation may comprise (A) worsening of two or more of the following major symptoms for at least two consecutive days: dyspnea, sputum volume and sputum purulence or (B) worsening of any one major symptom together with any one of the following minor symptoms for at least two consecutive days: sore throat, colds (nasal discharge and/or nasal congestion), fever (oral temperature>37.5° C.) without other cause and increased cough. For instance, a COPD exacerbation may comprise worsening of two or more of the major symptoms (dyspnea, sputum volume and sputum purulence) for at least two consecutive days.

A COPD exacerbation may be a moderate COPD exacerbation or a severe COPD exacerbation. A moderate exacerbation is defined as worsening symptoms of COPD (as defined above) requiring a minimum of three days of treatment with oral/systemic corticosteroids and/or antibiotics. A severe exacerbation is defined as worsening symptoms of COPD (as defined above) requiring in-patient hospitalization. The composition may reduce the severity of COPD exacerbations in a patient, and accordingly the composition may be for use in preventing severe COPD exacerbations in a patient. For instance, the patient may experience no severe COPD exacerbations in the year following first administration of the composition.

Regimen

A liquid pharmaceutical composition disclosed herein may be administered to a subject once, twice or three times a day, or may be administered twice, three times, four times or five times a week. For instance, the pharmaceutical composition may be administered twice a day.

The methods may comprise administering two doses of the (e.g., liquid) pharmaceutical composition comprising about 3 mg ensifentrine free base to a human subject per day by inhalation. The method may comprise administering a dose of about 3 mg of the pharmaceutical composition to the human subject twice a day (3 mg BID) by inhalation. In some instances, the method comprises administering by nebuliser a dose of about 3 mg the pharmaceutical composition to the human subject twice a day. Each dose may be 3.0 mg free base ensifentrine administered by nebulizer.

In some embodiments, the human subject may be male. In some embodiments, the human subject may be female. The human subject may have an age of greater than or equal to 65 years. The human subject may have an age of less than 65 years. The human subject may be taking a background medication selected from one or more of a long-acting muscarinic antagonist (LAMA), a long-acting beta-agonist (LABA) and an inhaled corticosteroid (ICS). In some embodiments, the human subject is taking a LAMA. In some embodiments, the human subject is taking a LABA. In some embodiments, the human subject is taking an ICS.

In some cases, the human subject is not receiving a background medication. For instance, the human subject may not be taking a background medication, which background medication is a long-acting muscarinic antagonist (LAMA), a long-acting beta-agonist (LABA) or an inhaled corticosteroid (ICS). In some embodiments, the human subject is not taking a LAMA. In some embodiments, the human subject is not taking a LABA. In some embodiments, the human subject is not taking an ICS.

The (e.g., liquid) pharmaceutical compositions may be used as a maintenance therapy. In some embodiments, the method comprises administering the pharmaceutical composition to the human subject at least once per day for at least 8 weeks. The pharmaceutical composition may be administered to the human subject at least once per day for at least 16 weeks or at least 24 weeks. The method may comprise administering the pharmaceutical composition to the human subject for at least 1 year. The method may comprise administering the composition to the human subject at least once every 24 hours, at least twice every 24 hours, for at least 8 weeks, for at least 16 weeks, or for at least 24 weeks.

Methods of Preparation

Provided herein are methods of producing the particulate composition described herein.

The process for producing the particulate composition may comprise reacting a compound of formula (IV) with 4-nitrophenyl chloroformate and ammonia, wherein the compound of formula (IV), 4-nitrophenyl chloroformate and ammonia are reacted in a solvent comprising dichloromethane,

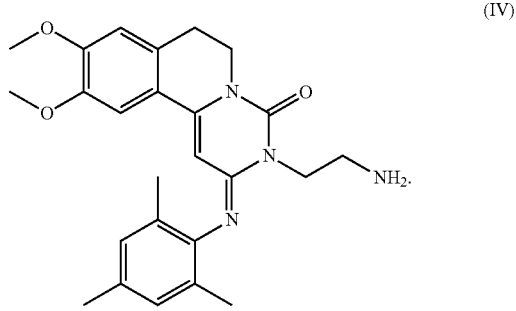 [SMILES: COc1cc2c(cc1OC)-c1c/c(=N\c3c(C)cc(C)cc3C)n(CCN)c(=O)n1CC2]

(IV)

The solvent may comprise dichloromethane and water. In some embodiments, the solvent comprises dichloromethane. In some embodiments, the solvent comprises water. For instance, the solvent may comprise from 30 to 60 vol % dichloromethane and from 30 to 60 vol % water, relative to the total volume of the solvent. The solvent may comprise about 30 vol %, about 35 vol %, about 40 vol %, about 45 vol %, about 50 vol %, about 55 vol %, or about 60 vol % of dichloromethane. The solvent may comprise about 30 vol %, about 35 vol %, about 40 vol %, about 45 vol %, about 50 vol %, about 55 vol %, or about 60 vol % of water. The solvent may comprise from 40 to 55 vol % dichloromethane and from 40 to 55 vol % water, relative to the total volume of the solvent. The total content of dichloromethane and water in the solvent is in some instances at least 90 vol % or at least 95 vol % based on the total volume of the solvent.

In some embodiments, 1 eqv of the compound of formula (IV) is reacted with from 0.8 to 1.5 eqvs of 4-nitrophenyl chloroformate. In some embodiments, the compound of formula (IV) is reacted with about 0.8 eqvs, about 0.85 eqvs, about 0.9 eqvs, about 0.95 eqvs, about 1 eqvs, about 1.05 eqvs, about 1.1 eqvs, about 1.15 eqvs, about 1.2 eqvs, about 1.25 eqvs, about 1.3 eqvs, about 1.35 eqvs, about 1.4 eqvs, about 1.45 eqvs, or about 1.5 eqvs of 4-nitrophenyl chloroformate. In some embodiments, the compound of formula (IV) may be reacted with from 1.0 to 1.2 eqvs of 4-nitrophenyl chloroformate.

In some embodiments, The compound of formula (IV) may be reacted with 4-nitrophenyl chloroformate and ammonia at a temperature of from 20 to 40° C. for at least 1 hour.

In some embodiments, The process may comprise: (i) combining the compound of formula (IV) with dichloromethane in a reactor; (ii) then adding an aqueous solution of a base to the reactor; (iii) then adding a solution of 4-nitrophenyl chloroformate in dichloromethane to the reactor; and (iv) then adding a solution of ammonia to the reactor. In some embodiments, the solution of ammonia is an aqueous solution of ammonia, for instance 25% aqueous ammonia. The base in step (ii) is in some embodiments potassium bicarbonate.

In some instances, the process comprises combining the compound of formula (IV) with dichloromethane in a reactor. In some instances, the process comprises adding an aqueous solution of a base to the reactor. In some instances, the process comprises adding a solution of 4-nitrophenyl chloroformate in dichloromethane to the reactor. In some instances, the process comprises adding a solution of ammonia to the reactor.

In some embodiments, the organic phase product of steps (i) to (iv) is isolated, concentrated and then combined with methanol to produce a suspension of the particulate composition. The process may further comprise drying, recrystallisation and optionally particle size reduction of the particulate composition.

The disclosure is described in more detail by the following Examples.

EXAMPLES

Methods

Ultra-High Performance Liquid Chromatography (UPLC)
  Column: Acquity UPLC BEH Phenyl 100 mm×2.1 mm, 1.7 μm
  Detector Wavelength: 254 nm
  Retractive index detector sensitivity: N/AP
  Retractive index detector temperature: N/AP
  Column temperature: 35° C.
  Autosampler temperature: N/AP
  Flow: 0.53 mL/min
  Injection volume: 1 μL
  Run time: 11.10 min Gradient program:

| Time (min) | % Mobile Phase A | % Mobile Phase B |
|---|---|---|
| 0 | 97 | 3 |
| 2.27 | 70 | 30 |
| 4.86 | 55 | 45 |
| 6.48 | 5 | 95 |
| 7.45 | 5 | 95 |
| 8.1 | 97 | 3 |
| 11.1 | 97 | 3 |

Mobile Phase, Washing Solutions and Dissolution Mixture

Mobile Phase A: Water/trifluoroacetic acid (100/0.1, v/v) (Accurately transfer 1000 mL of water and 1 mL of trifluoroacetic acid into a suitable flask, mix well and degas prior to use.)

Mobile Phase B: Acetonitrile/trifluoroacetic acid (100/0.1, v/v) (Accurately transfer 1000 mL of acetonitrile and 1 mL of trifluoroacetic acid into a suitable flask, mix well and degas prior to use.)

Dissolution Mixture (diluent): Acetonitrile/Water (50/50, v/v) (Transfer 500 mL acetonitrile into a suitable flask and add 500 mL of water. Mix well to homogenize and degas prior to use.)

Needle Wash: Acetonitrile/Water (50/50, v/v) (Transfer 500 mL of acetonitrile into a suitable flask and add 500 mL of water. Mix well to homogenize and degas prior to use.)

Seal and Column Wash: Acetonitrile/Water (10/90, v/v) (Transfer 900 mL of water into a suitable flask and add 100 mL of acetonitrile. Mix well to homogenize and degas prior to use.)

Equipment Wash (column storage): Acetonitrile/Water (90/10, v/v) (Transfer 900 mL of acetonitrile into a suitable flask and add 100 mL of water. Homogenize and degas prior to use.)

Example 1—Preparation of Ensifentrine

Preparation of (E)-3-(2-aminoethyl)-2-(mesitylimino)-9,10-dimethoxy-2,3,6,7-tetrahydro-4H-pyrimido[6,1-a]isoquinolin-4-one

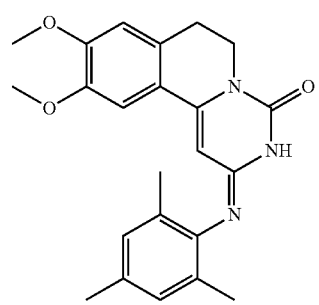

(I)

A mixture of 10 g of compound (I), 3.21 g of lithium carbonate, 155 mL of acetonitrile and 4.29 g of bromoacetonitrile was refluxed until the reaction was completed. The solids were removed by filtration and the filtrate solution was concentrated by distillation under reduced pressure with the addition of tetrahydrofuran. The solid product formed was isolated by filtration.

NMR and single crystal X-ray diffraction analysis showed that the product was a cyclic ammonium bromide salt (II) with the following structure.

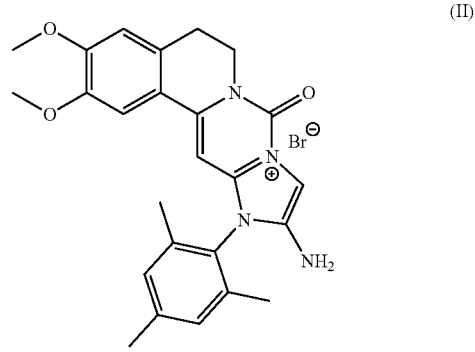 [SMILES: COc1cc2c(cc1OC)-c1cc3n(-c4c(C)cc(C)cc4C)c(N)c[n+]3c(=O)n1CC2 ; [Br-]]

(II)

Under hydrogenation conditions using Raney Ni and 7N methanolic ammonia, the cyclic ammonium bromide salt (II) ring-opened to produce (E)-2-(2-(mesitylimino)-9,10-dimethoxy-4-oxo-6,7-dihydro-2H-pyrimido[6,1-a]isoquinolin-3(4H)-yl)acetonitrile (compound (III))

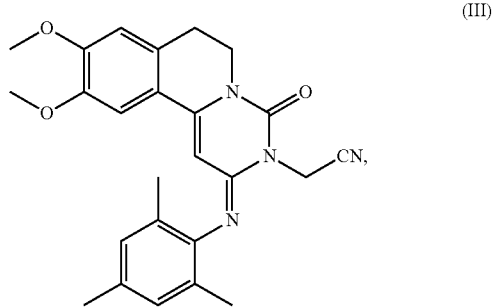 [SMILES: COc1cc2c(cc1OC)-c1c/c(=N\c3c(C)cc(C)cc3C)n(CC#N)c(=O)n1CC2]

(III)

which was reduced in situ to produce (E)-3-(2-aminoethyl)-2-(mesitylimino)-9,10-dimethoxy-2,3,6,7-tetrahydro-4H-pyrimido[6,1-a]isoquinolin-4-one (compound (IV)).

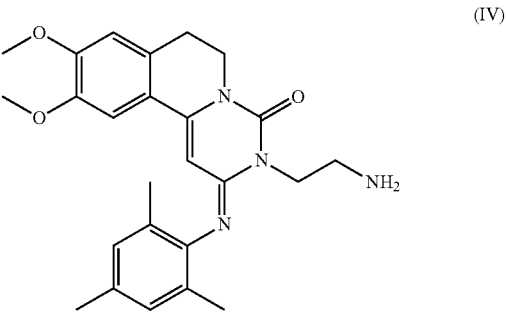 [SMILES: COc1cc2c(cc1OC)-c1c/c(=N\c3c(C)cc(C)cc3C)n(CCN)c(=O)n1CC2]

(IV)

Production of Ensifentrine from Compound (IV) Using Sodium Cyanate

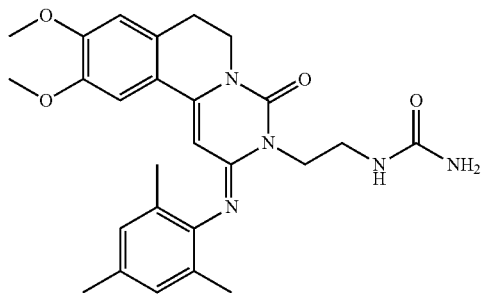

(V)

Compound (IV) was converted to ensifentrine (compound (V)) with sodium cyanate using the following procedure. 70.4 mL of methanol was added to 8.0 g of compound (IV). A solution of 1.80 g of sodium cyanate (1.5 eq) in 18.4 mL of deionized water (2.3 vol) was added over thirty minutes. The mixture was heated to between 55 and 65° C. A solution of 1.68 mL hydrochloric acid (1.1 eq) and 24.0 mL deionized water (3 vol) was added over 15 minutes, while maintaining the temperature between 55 and 65° C. The suspension was stirred at reflux for at least two hours. The suspension was cooled to between 0 and 5° C. and stirred for an hour. The suspension was filtered and the cake was washed with deionized water. The cake was then dried under vacuum to produce the product.

The product obtained was analysed by UPLC. The composition of the product is set out in Table 1 below.

TABLE 1

| RRT | Area (%) | Species |
|---|---|---|
| 0.78 | 0.63 | (E)-3-(2-aminoethyl)-2-(mesitylimino)-9,10-dimethoxy-2,3,6,7-tetrahydro-4H-pyrimido[6,1-a]isoquinolin-4-one (compound (IV)) |
| 0.84 | 0.07 | (E)-1-(2-(10-hydroxy-2-(mesitylimino)-9-methoxy-4-oxo-6,7-dihydro-2H-pyrimido[6,1-a]isoquinolin-3(4H)-yl)ethyl) urea (10-des-methyl) |
| 0.86 | 0.07 | (E)-1-(2-(9-hydroxy-2-(mesitylimino)-10-methoxy-4-oxo-6,7-dihydro-2H-pyrimido[6,1-a]isoquinolin-3(4H)-yl)ethyl)urea (9-des-methyl) |
| 0.96 | 0.20 | (E)-2-(mesitylimino)-9,10-dimethoxy-2,3,6,7-tetrahydro-4H-pyrimido [6,1-a]isoquinolin-4-one (compound (I)) |
| 0.98 | 0.76 | biuret impurity |
| 1.00 | 97.03 | ensifentrine |
| 1.31 | 0.09 | 1,3-bis(2-((E)-2-(mesitylimino)-9,10-dimethoxy-4-oxo-6,7-dihydro-2H-pyrimido[6,1-a]isoquinolin-3(4H)-yl) ethyl) urea (BMIQU) |

The biuret impurity (RRT 0.98) could not readily be removed by recrystallisation.

The structures of the impurities are shown below.

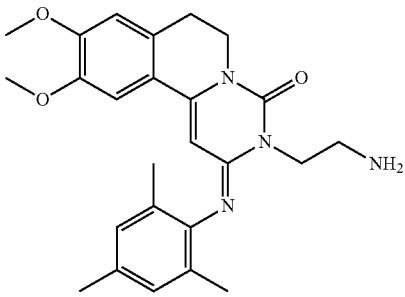 [SMILES: COc1cc2c(cc1OC)-c1c/c(=N\c3c(C)cc(C)cc3C)n(CCN)c(=O)n1CC2]

(E)-3-(2-aminoethyl)-2-(mesitylimino)-9,10-dimethoxy-2,3,6,7-tetrahydro-4H-pyrimido[6,1-a]isoquinolin-4-one (compound (IV)) [RRT 0.78]

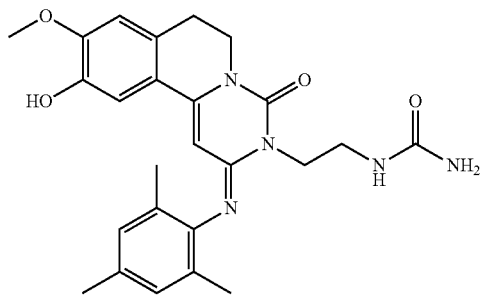 [SMILES: COc1cc2c(cc1O)-c1c/c(=N\c3c(C)cc(C)cc3C)n(CCNC(N)=O)c(=O)n1CC2]

(E)-1-(2-(10-hydroxy-2-(mesitylimino)-9-methoxy-4-oxo-6,7-dihydro-2H-pyrimido[6,1-a]isoquinolin-3(4H)-yl)ethyl)urea (10-des-methyl) [RRT 0.84]

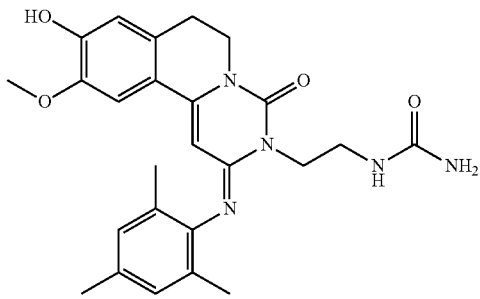 [SMILES: COc1cc2c(cc1O)CCn1c-2c/c(=N\c2c(C)cc(C)cc2C)n(CCNC(N)=O)c1=O]

(E)-1-(2-(9-hydroxy-2-(mesitylimino)-10-methoxy-4-oxo-6,7-dihydro-2H-pyrimido[6,1-a]isoquinolin-3(4H)-yl)ethyl)urea (9-des-methyl) [RRT 0.86]

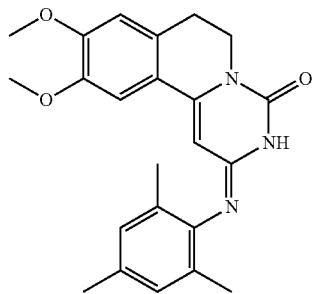 [SMILES: COc1cc2c(cc1OC)-c1c/c(=N\c3c(C)cc(C)cc3C)[nH]c(=O)n1CC2]

(E)-2-(mesitylimino)-9,10-dimethoxy-2,3,6,7-tetrahydro-4H-pyrimido[6,1-a]isoquinolin-4-one (compound (I)) [RRT 0.96]

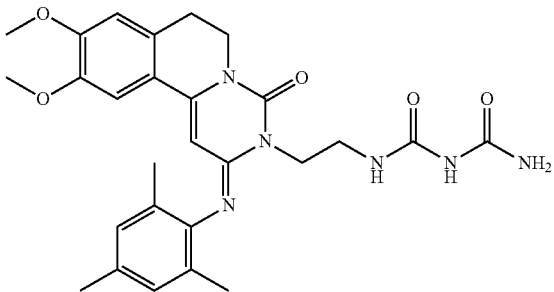 [SMILES: COc1cc2c(cc1OC)-c1c/c(=N\c3c(C)cc(C)cc3C)n(CCNC(=O)NC(N)=O)c(=O)n1CC2]

biuret impurity [RRT 0.98]

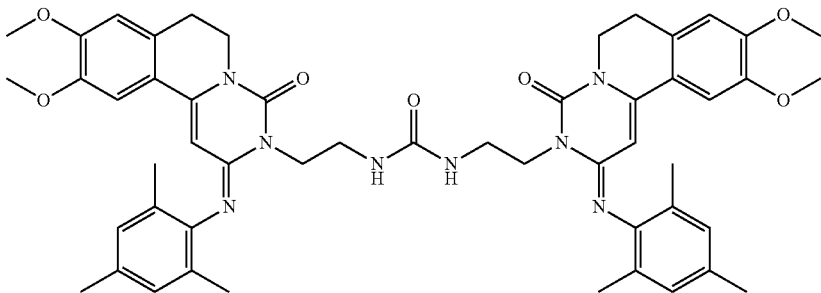

1,3-bis(2-((E)-2-(mesitylimino)-9,10-dimethoxy-4-oxo-6,7-dihydro-2H-pyrimido[6,1-a]isoquinolin-3(4H)-yl)ethyl)urea (BMIQU) [RRT 1.31]

Production of Ensifentrine from Compound (IV) Using Nitrophenyl Chloroformate and Ammonia Compound (IV) was converted to ensifentrine with nitrophenyl chloroformate and ammonia using the following procedure. 660.0 mL of dichloromethane (5 vol) was added to a reactor with 132.0 g of compound (IV). A solution of 153.12 g of potassium bicarbonate in 1320.0 mL of deionized water (10 vol) was added to the reactor and the mixture was called to a temperature between 0 and 5° C. A solution of 660.0 mL of dichloromethane (5 vol) and 73.47 g of 4-nitrophenyl chloroformate (1.2 eq) was then added, keeping the temperature between 0 and 10° C. The mixture was then stirred at a temperature of between 5 and 10° C. for at least 2 hours before addition of 1320.0 mL of 25% aqueous ammonia (10 vol). The mixture was then stirred at a temperature of between 25 and 35° C. overnight. Stirring was stopped and the phases were allowed to separate for at least 15 minutes. The organic phase contained the product. The aqueous phase was extracted with 660 mL dichloromethane and the combined organic phases washed with 660 mL of deionized water. The organic phase was filtered and the reactor and filter were washed with 132.0 mL of dichloromethane.

The filtrate was then concentrated, before addition of methanol. The resulting suspension was heated and stirred. The suspension was cooled to a temperature of 15 to 25° C. and the suspension was filtered. The filter cake was washed with methanol before being dried under vacuum to obtain the product.

The product obtained was analysed by UPLC. The composition of the product is set out in Table 2 below.

TABLE 2

| RRT | Area (%) | Species |
| --- | --- | --- |
| 0.78 | 0.01 | (E)-3-(2-aminoethyl)-2-(mesitylimino)-9,10-dimethoxy-2,3,6,7-tetrahydro-4H-pyrimido[6,1-a]isoquinolin-4-one (compound (IV)) |
| 0.84 | 0.07 | (E)-1-(2-(10-hydroxy-2-(mesitylimino)-9-methoxy-4-oxo-6,7-dihydro-2H-pyrimido[6,1-a]isoquinolin-3(4H)-yl)ethyl)urea (10-des-methyl) |
| 0.86 | 0.07 | (E)-1-(2-(9-hydroxy-2-(mesitylimino)-10-methoxy-4-oxo-6,7-dihydro-2H-pyrimido[6,1-a]isoquinolin-3(4H)-yl)ethyl] urea (9-des-methyl) |
| 0.96 | 0.00 | (E)-2-(mesitylimino)-9,10-dimethoxy-2,3,6,7-tetrahydro-4H-pyrimido[6,1-a]isoquinolin-4-one (compound (I)) |
| 0.98 | 0.02 | biuret impurity |
| 1.00 | 98.55 | ensifentrine |
| 1.31 | 0.51 | 1,3-bis(2-((E)-2-(mesitylimino)-9,10-dimethoxy-4-oxo-6,7-dihydro-2H-pyrimido[6,1-a]isoquinolin-3(4H)-yl)ethyl)urea(BMIQU) |

Only very low quantities of the biuret impurity (RRT 0.98) were generated.

Example 2—Preparation of a Larger Batch of Ensifentrine

A larger batch of ensifentrine was produced using 4-nitrophenyl chloroformate and ammonia. The drug substance obtained was analysed by UPLC. The main impurities present in the drug substance are set out in Table 3 below.

TABLE 3

| Area (%) | Species |
| --- | --- |
| 0.02 | (E)-1-(2-(10-hydroxy-2-(mesitylimino)-9-methoxy-4-oxo-6,7-dihydro-2H-pyrimido[6,1-a]isoquinolin-3(4H)-yl)ethyl)urea (10-des-methyl impurity) |
| 0.08 | (E)-1-(2-(9-hydroxy-2-(mesitylimino)-10-methoxy-4-oxo-6,7-dihydro-2H-pyrimido[6,1-a]isoquinolin-3(4H)-yl)ethyl)urea (9-des-methyl impurity) |
| 0.02 | biuret impurity |
| 99.80 | ensifentrine |
| 0.04 | 1,3-bis(2-((E)-2-(mesitylimino)-9,10-dimethoxy-4-oxo-6,7-dihydro-2H-pyrimido[6,1-a]isoquinolin-3(4H)-yl)ethyl)urea (BMIQU) |

Example 3—Preparation of Aqueous Suspension Formulation

The drug substance obtained from Example 2 was micronised and dry heat treated at 16000 for at least 120 minutes to produced sterilised ensifentrine particles. The sterilised ensifentrine particles obtained by dry heat treatment were combined with a suspension vehicle under aseptic conditions to obtain a sterile suspension formulation comprising ensifentrine, having the composition shown in Table 4.

TABLE 4

| Constituent | Concentration (mg/mL) |
| --- | --- |
| Sterilised ensifentrine particles (RPL554) | 1.2 |
| Polysorbate 20 (Tween 20) | 0.50 |
| Sorbitan Monolaurate (Span 20) | 0.05 |
| Sodium Dihydrogen Phosphate Dihydrate | 0.744 |
| Disodium Hydrogen Phosphate Dihydrate | 0.853 |
| Sodium Chloride | 8.60 |
| Water | q.s. to 1 mL |

The suspension formulation was assessed by HPLC and the content of the impurity bis-(mesitylisoquinolinone)urea (BMIQU) was found to be no greater than 0.6 wt % relative to the total amount of ensifentrine in the suspension formulation.

EMBODIMENTS

The following are exemplary embodiments of the disclosure herein:
 1. A particulate composition comprising ensifentrine, wherein the particulate composition further comprises:

from greater than 0.00 wt % to 0.60 wt % of 1,3-bis(2-(2-(mesitylimino)-9,10-dimethoxy-4-oxo-6,7-dihydro-2H-pyrimido[6,1-a]isoquinolin-3(4H)-yl)ethyl)urea (BMIQU) relative to the total weight of ensifentrine; and from 0.00 wt % to 0.50 wt % of a biuret impurity of formula (A) relative to the total weight of ensifentrine:

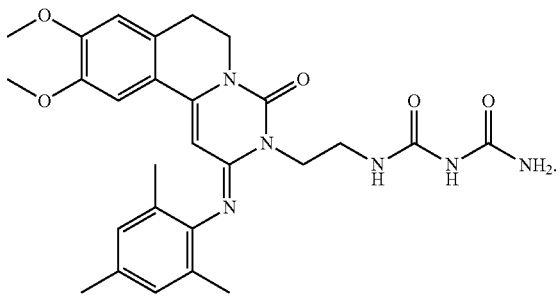
(A)

2. The particulate composition according to embodiment 1, wherein the particulate composition comprises from 0.00 wt % to 0.30 wt % of the biuret impurity relative to the total weight of ensifentrine.

3. The particulate composition according to embodiment 1 or embodiment 2, wherein the particulate composition comprises from 0.00 wt % to 0.05 wt % of the biuret impurity relative to the total weight of ensifentrine.

4. The particulate composition according to any one of the preceding embodiments, wherein the particulate composition comprises from 0.01 wt % to 0.30 wt % of BMIQU relative to the total weight of ensifentrine.

5. The particulate composition according to any one of the preceding embodiments, wherein the particulate composition comprises from 0.02 wt % to 0.06 wt % of BMIQU relative to the total weight of ensifentrine.

6. The particulate composition according to any one of the preceding embodiments, wherein the particulate composition further comprises:
from greater than 0.00 wt % to 0.10 wt % of 1-(2-(9-hydroxy-2-(mesitylimino)-10-methoxy-4-oxo-6,7-dihydro-2H-pyrimido[6,1-a]isoquinolin-3(4H)-yl)ethyl)urea (9-des-methyl impurity); and/or
from greater than 0.00 wt % to 0.10 wt % of 1-(2-(10-hydroxy-2-(mesitylimino)-9-methoxy-4-oxo-6,7-dihydro-2H-pyrimido[6,1-a]isoquinolin-3(4H)-yl)ethyl)urea (10-des-methyl impurity).

7. The particulate composition according to any one of the preceding embodiments, wherein the particulate composition comprises at least 98.0 wt % of ensifentrine relative to the total weight of the particulate composition.

8. The particulate composition according to any one of the preceding embodiments, wherein the particulate composition comprises at least 99.0 wt % of ensifentrine relative to the total weight of the particulate composition, optionally at least 99.2 wt % of ensifentrine relative to the total weight of the particulate composition.

9. The particulate composition according to any one of the preceding embodiments, wherein the particulate composition comprises:
from 99.4 to 99.9 wt % of ensifentrine;
from 0.01 wt % to 0.30 wt % of BMIQU;
from 0.00 wt % to 0.10 wt % of the biuret impurity;
from 0.01 wt % to 0.20 wt % of the 9-des-methyl impurity; and
from 0.01 wt % to 0.20 wt % of the 10-des-methyl impurity,
wherein the wt % is relative to the total weight of the particulate composition.

10. A particulate composition according to any one of the preceding embodiments, wherein the particulate composition comprises:
from 99.5 to 99.9 wt % of ensifentrine;
from 0.02 wt % to 0.10 wt % of BMIQU;
from 0.00 wt % to 0.04 wt % of the biuret impurity;
from 0.01 wt % to 0.10 wt % of the 9-des-methyl impurity; and
from 0.01 wt % to 0.10 wt % of the 10-des-methyl impurity,
wherein the wt % is relative to the total weight of the particulate composition.

11. The particulate composition according to any one of the preceding embodiments, wherein the particulate composition consists of:
from 99.6 to 99.9 wt % of ensifentrine;
from 0.02 wt % to 0.10 wt % of BMIQU;
from 0.00 wt % to 0.04 wt % of the biuret impurity;
from 0.01 wt % to 0.10 wt % of the 9-des-methyl impurity;
from 0.01 wt % to 0.10 wt % of the 10-des-methyl impurity; and
no greater than 0.36 wt % total of other related substances,
wherein the wt % is relative to the total weight of the particulate composition.

12. The particulate composition according to any one of the preceding embodiments, wherein the particulate composition has a Dv50 of from about 0.2 to about 5.0 µm.

13. The particulate composition according to embodiment 12, wherein the particulate composition has a Dv50 of from about 1.0 µm to about 2.2 µm.

14. The particulate composition according to any one of the preceding embodiments, wherein the particulate composition has a Dv10 of from about 0.3 µm to about 0.9 µm and/or a Dv90 of from about 2.3 µm to about 4.5 µm.

15. A liquid pharmaceutical composition suitable for administration by inhalation comprising (a) the particulate composition as defined in any one of the preceding embodiments and (b) a diluent.

16. The liquid pharmaceutical according to embodiment 15, wherein the particulate composition is suspended in the diluent.

17. The liquid pharmaceutical composition according to embodiment 15 or embodiment 16,
wherein the liquid pharmaceutical composition comprises no more than 1.00 wt % of BMIQU relative to the total weight of ensifentrine.

18. The liquid pharmaceutical composition according to embodiment 17,
wherein the liquid pharmaceutical composition comprises no more than 0.50 wt % of BMIQU relative to the total weight of ensifentrine.

19. The liquid pharmaceutical composition according to any one of embodiments 15 to 18, wherein the liquid pharmaceutical composition comprises, relative to the total weight of the liquid pharmaceutical composition:
a) the particulate composition at a concentration of from 0.8 to 1.6 mg/mL;
b) one or more surfactants at a total concentration of from 0.1 to 1.0 mg/mL;
c) one or more buffers at a total concentration of from 1.0 to 2.0 mg/ml; and
d) water.

20. The liquid pharmaceutical composition according to any one of embodiments 15 to 19, wherein the liquid pharmaceutical composition comprises, relative to the total weight of the liquid pharmaceutical composition:
   a) the particulate composition at a concentration of from 1.0 to 1.4 mg/mL;
   b) polysorbate 20 (Tween 20) at a concentration of 0.3 to 0.7 mg/mL;
   c) sorbitan monolaurate (Span 20) at a concentration of 0.0 to 0.1 mg/mL;
   d) sodium dihydrogen phosphate dihydrate at a concentration of 0.5 to 1.0 mg/mL;
   e) disodium hydrogen phosphate dihydrate at a concentration of 0.5 to 1.0 mg/mL;
   f) sodium chloride at a concentration of 5 to 10 mg/mL; and
   g) water.
21. The liquid pharmaceutical composition according to any one of embodiments 15 to 20, wherein the liquid pharmaceutical composition comprises from about 2.0 mg to about 4.0 mg of the particulate composition.
22. The liquid pharmaceutical composition according to any one of embodiments 15 to 21, wherein the liquid pharmaceutical composition is a suspension comprising, relative to the total weight of the liquid pharmaceutical composition:
   a) 1.2 mg/mL ensifentrine;
   b) 0.5 mg/ml polysorbate 20;
   c) 0.05 mg/ml sorbitan monolaurate;
   d) 0.744 mg/ml sodium dihydrogen phosphate;
   e) 0.853 mg/ml disodium hydrogen phosphate;
   f) 8.6 mg/ml sodium chloride; and
   g) water.
23. A method of:
   a) treating moderate chronic obstructive pulmonary disease (COPD),
   b) treating severe COPD,
   c) increasing trough lung function, or
   d) reducing frequency of an exacerbation of COPD;
      in a human subject in need thereof, the method comprising administering to the human subject via inhalation the particulate composition of any one of embodiments 1-14 or the liquid pharmaceutical composition of any one of embodiments 15-22.
24. A process for producing a particulate composition as defined in any one of embodiments 1 to 14, the process comprising:
   reacting a compound of formula (IV) with 4-nitrophenyl chloroformate and ammonia, wherein the compound of formula (IV), 4-nitrophenyl chloroformate and ammonia are reacted in a solvent comprising dichloromethane,

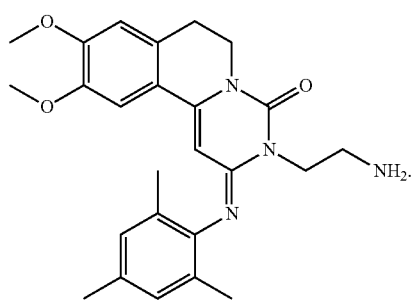

(IV)

25. The process according to embodiment 24, wherein 1 eqv of the compound of formula (IV) is reacted with from 0.8 to 1.5 eqvs of 4-nitrophenyl chloroformate, optionally with from 1.0 to 1.2 eqvs of 4-nitrophenyl chloroformate.
26. The process according to embodiment 24 or embodiment 25, wherein the process comprises:
   (i) combining the compound of formula (IV) with dichloromethane in a reactor;
   (ii) adding an aqueous solution of a base to the reactor;
   (iii) adding a solution of 4-nitrophenyl chloroformate in dichloromethane to the reactor; and
   (iv) adding a solution of ammonia to the reactor.
27. The process according to embodiment 26, wherein the base of (ii) is potassium bicarbonate.
28. A kit comprising the particulate composition of any one of embodiments 1-14 or the liquid pharmaceutical composition of any one of embodiments 15-22.

The invention claimed is:

1. A particulate composition comprising ensifentrine, wherein the particulate composition further comprises from about 0.01 wt % to about 1.0 wt % of 1,3-bis(2-(2-(mesitylimino)-9,10-dimethoxy-4-oxo-6,7-dihydro-2H-pyrimido[6,1-a]isoquinolin-3(4H)-yl)ethyl)urea (BMIQU) relative to the total weight of ensifentrine.

2. A particulate composition as claimed in claim 1, further comprising a biuret impurity of formula (A):

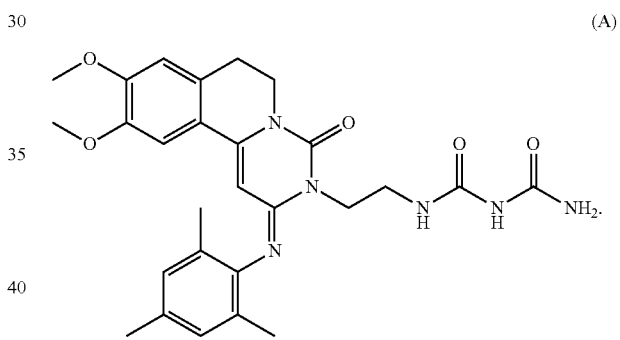

(A)

3. A particulate composition as claimed in claim 1, wherein there is no detectable biuret impurity of formula (A):

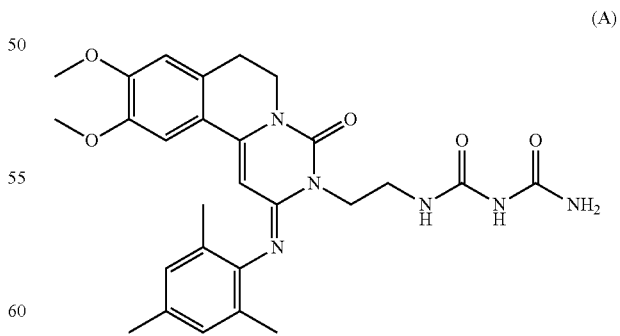

(A)

based on HPLC measurement.

4. A particulate composition as claimed in claim 2, wherein there is from 0.01 wt % to 1.0 wt % of the biuret impurity of formula (A) relative to the total weight of ensifentrine.

5. The particulate composition of claim 4, wherein the amount of biuret impurity (A) is from 0.01 wt % to 0.30 wt % relative to the total weight of ensifentrine.

6. The particulate composition of claim 5, wherein the amount of biuret impurity (A) is from 0.01 wt % to 0.10 wt % relative to the total weight of ensifentrine.

7. The particulate composition of claim 6, wherein the amount of biuret impurity (A) is from 0.01 wt % to 0.05 wt % relative to the total weight of ensifentrine.

8. The particulate composition of claim 1, wherein the particulate composition comprises from 0.01 wt % to 0.30 wt % of BMIQU relative to the total weight of ensifentrine.

9. The particulate composition of claim 8, wherein the particulate composition comprises from 0.02 wt % to 0.10 wt % of BMIQU relative to the total weight of ensifentrine.

10. The particulate composition of claim 1, wherein the particulate composition further comprises:
    from greater than 0.00 wt % to 0.10 wt % of 1-(2-(9-hydroxy-2-(mesitylimino)-10-methoxy-4-oxo-6,7-dihydro-2H-pyrimido[6,1-a]isoquinolin-3(4H)-yl)ethyl) urea (9-des-methyl impurity); or
    from greater than 0.00 wt % to 0.10 wt % of 1-(2-(10-hydroxy-2-(mesitylimino)-9-methoxy-4-oxo-6,7-dihydro-2H-pyrimido[6,1-a]isoquinolin-3(4H)-yl)ethyl) urea (10-des-methyl impurity).

11. The particulate composition of claim 1, wherein the particulate composition comprises at least 98.0 wt % of ensifentrine relative to the total weight of the particulate composition.

12. The particulate composition of claim 10, wherein the particulate composition comprises at least 99.0 wt % of ensifentrine relative to the total weight of the particulate composition, optionally at least 99.2 wt % of ensifentrine relative to the total weight of the particulate composition.

13. The particulate composition of claim 1, wherein the particulate composition comprises:
    from 99.4 to 99.9 wt % of ensifentrine;
    from 0.01 wt % to 0.30 wt % of BMIQU;
    from 0.01 wt % to 0.10 wt % of the biuret impurity;
    from 0.01 wt % to 0.20 wt % of the 9-des-methyl impurity; and
    from 0.01 wt % to 0.20 wt % of the 10-des-methyl impurity,
wherein the wt % is relative to the total weight of the particulate composition.

14. A particulate composition of claim 13, wherein the particulate composition comprises:
    from 99.5 to 99.9 wt % of ensifentrine;
    from 0.02 wt % to 0.10 wt % of BMIQU;
    from 0.01 wt % to 0.04 wt % of the biuret impurity;
    from 0.01 wt % to 0.10 wt % of the 9-des-methyl impurity; and
    from 0.01 wt % to 0.10 wt % of the 10-des-methyl impurity,
wherein the wt % is relative to the total weight of the particulate composition.

15. The particulate composition of claim 13, wherein the particulate composition consists of:
    from 99.6 to 99.9 wt % of ensifentrine;
    from 0.02 wt % to 0.10 wt % of BMIQU;
    from 0.01 wt % to 0.04 wt % of the biuret impurity;
    from 0.01 wt % to 0.10 wt % of the 9-des-methyl impurity;
    from 0.01 wt % to 0.10 wt % of the 10-des-methyl impurity; and
    no greater than 0.36 wt % total of other related substances,
wherein the wt % is relative to the total weight of the particulate composition.

16. The particulate composition of claim 1, wherein the particulate composition has a Dv50 of from about 0.2 to about 5.0 μm.

17. The particulate composition of claim 15, wherein the particulate composition has a Dv50 of from about 1.0 μm to about 2.2 μm.

18. The particulate composition of claim 1, wherein the particulate composition has a Dv10 of from about 0.3 μm to about 0.9 μm or a Dv90 of from about 2.3 μm to about 4.5 μm.

19. A liquid pharmaceutical composition suitable for administration by inhalation comprising (a) the particulate composition of claim 1; and (b) a diluent.

20. The liquid pharmaceutical of claim 18, wherein the particulate composition is suspended in the diluent.

21. The liquid pharmaceutical composition of claim 18, wherein the liquid pharmaceutical composition comprises no more than 1.0 wt % of BMIQU relative to the total weight of ensifentrine.

22. The liquid pharmaceutical composition of claim 20, wherein the liquid pharmaceutical composition comprises no more than 0.50 wt % of BMIQU relative to the total weight of ensifentrine.

23. The liquid pharmaceutical composition of claim 21, wherein the liquid pharmaceutical composition comprises:
    a) the particulate composition at a concentration of from 0.8 to 1.6 mg/mL;
    b) one or more surfactants at a total concentration of from 0.1 to 1.0 mg/mL;
    c) one or more buffers at a total concentration of from 1.0 to 2.0 mg/ml; and
    d) water.

24. The liquid pharmaceutical composition of claim 22, wherein the liquid pharmaceutical composition comprises:
    a) the particulate composition at a concentration of from 1.0 to 1.4 mg/mL;
    b) polysorbate 20 at a concentration of 0.3 to 0.7 mg/mL;
    c) sorbitan monolaurate at a concentration of 0.0 to 0.1 mg/mL;
    d) sodium dihydrogen phosphate dihydrate at a concentration of 0.5 to 1.0 mg/mL;
    e) disodium hydrogen phosphate dihydrate at a concentration of 0.5 to 1.0 mg/mL;
    f) sodium chloride at a concentration of 5 to 10 mg/mL; and
    g) water.

25. The liquid pharmaceutical composition of claim 19, wherein the liquid pharmaceutical composition comprises from about 2.0 mg to about 4.0 mg of the particulate composition.

26. The liquid pharmaceutical composition of claim 23, wherein the liquid pharmaceutical composition is a suspension comprising:
    a) 1.2 mg/mL ensifentrine;
    b) 0.5 mg/ml polysorbate 20;
    c) 0.05 mg/ml sorbitan monolaurate;
    d) 0.744 mg/ml sodium dihydrogen phosphate dihydrate;
    e) 0.853 mg/ml disodium hydrogen phosphate dihydrate;
    f) 8.6 mg/ml sodium chloride; and
    g) water.

* * * * *